(12) United States Patent
Lindner et al.

(10) Patent No.: US 6,313,247 B1
(45) Date of Patent: Nov. 6, 2001

(54) CINCHONAN BASED CHIRAL SELECTORS FOR SEPARATION OF STEREOISOMERS

(76) Inventors: Wolfgang Lindner, St. Veiter Anger 22, Graz (AT), 8046; Michael Laemmerhofer, Neustiftgasse 66/3, Vienna (AT), 1070; Norbert Maier, Dietersdorf 19, Wundschuh (AT), 8142

( * ) Notice: Subject to any disclaimer, the term of this patent is extended or adjusted under 35 U.S.C. 154(b) by 0 days.

(21) Appl. No.: 09/194,892

(22) PCT Filed: Jun. 4, 1997

(86) PCT No.: PCT/EP97/02888

§ 371 Date: Nov. 17, 1999

§ 102(e) Date: Nov. 17, 1999

(87) PCT Pub. No.: WO97/46557

PCT Pub. Date: Dec. 11, 1997

(30) Foreign Application Priority Data

Jun. 5, 1996 (EP) .................................................. 96109072

(51) Int. Cl.[7] .......................... C07D 453/04; A61K 31/47
(52) U.S. Cl. .......................... 526/259; 546/134; 546/136; 106/490; 428/404; 428/407
(58) Field of Search ............................ 526/259; 546/134, 546/136; 106/490; 428/404, 407

(56) References Cited

FOREIGN PATENT DOCUMENTS

| 0044984 | 2/1982 | (EP) . |
| WO/92/20677 | 11/1992 | (WO) . |

OTHER PUBLICATIONS

Lämmerhofer, M., et al. (1996) "Quinine and quinidine derivatives as chiral selectors—I. Brush type chiral stationary phases for high–performance liquid chromatography based on chinchonan carbamates and their application as chiral anion exchangers", *Journal of Chromatography A*, 741:33–48.

Ben Hassine B. et al.: "Asymmetric synthesis and potential asymmetric of α–amino alcohols: hydroxyamination of olefins by the sharpless method", Chemical Abstracts, vol. 106, No. 3, Jan. 19, 1987, Abstract No. 17586a.

*Primary Examiner*—Donald R. Wilson
(74) *Attorney, Agent, or Firm*—Townsend & Townsend & Crew LLP

(57) ABSTRACT

Enantioseparation methods using chemical compounds which contain the chiral 9,11-substituted-10,11-dihydro-cinchonan skeleton (9,11-Subst.-DHC) and the precursors thereof with the 9-substituted cinchonan skeleton (9-Subst.-C) are described and discussed. The chiral compounds of the present invention are based on cinchonan derivatives containing amide structure elements which support effectively and co-operatively the enantioseparation of chiral acidic selectands involving also ion-pair and ion-exchange binding mechanism between the strong amino group of the selector and the acidic group of the selectand. The methods of enantioseparation of the present invention are related to stereoselective liquid-liquid and liquid-solid type extraction principles and fractionated crystallization employing cinchonan derivative type selectors. In one embodiment of the present invention the chiral selector is immobilized onto support material or is incorporated within a polymer or is part of a polymer used for liquid-solid enantioseparation techniques.

5 Claims, 10 Drawing Sheets

9,11-Substituted-10,11-dihydrocinchonan skeleton
9,11-Subst.-DHC skeleton

9-Substituted-cinchonan skeleton
9-Subst.-C skeleton

| Alkaloid | $R_2$ | Configurations |
|---|---|---|
| Quinine (QN) | $-OCH_3$ | (1S, 3R, 4S, 8S, 9R) |
| Quinidine (QD) | $-OCH_3$ | (1S, 3R, 4S, 8R, 9S) |
| Epi-Quinine (eQN) | $-OCH_3$ | (1S, 3R, 4S, 8S, 9S) |
| Epi-Quinidine (eQD) | $-OCH_3$ | (1S, 3R, 4S, 8R, 9R) |
| Cinchonidine (CD) | -H | (1S, 3R, 4S, 8S, 9R) |
| Cinchonine (CN) | -H | (1S, 3R, 4S, 8R, 9S) |
| Epi-Cinchonidine (eCD) | -H | (1S, 3R, 4S, 8S, 9S) |
| Epi-Cinchonine (eCN) | -H | (1S, 3R, 4S, 8R, 9R) |

Quaternized 9,11-subst.-DHC-based CSPs

| CSP | R₁ | R₆ |
|---|---|---|
| Quinidine carbamate CSPs (1S, 3R, 4S, 8R, 9S) (CQD) | | |
| CSP XIa | decyl | methyl |
| CSP XIb | decyl | hydrogen |

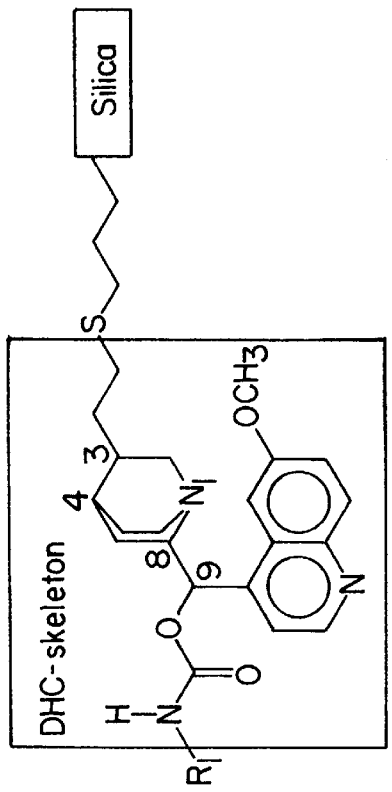
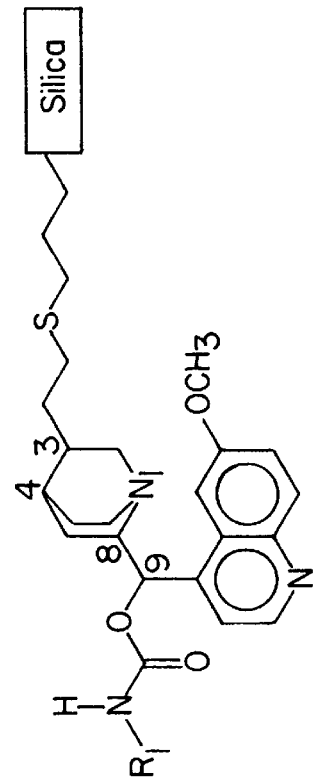

FIG. 10.

| CSP | R₁ |
|---|---|
| 9, 11-subst.-10, 11-dihydroquinine carbanate CSPs | |
| CSP I | t.-butyl |
| CSP II | 3,5-dinitrophenyl |
| CSP IV | 2,6-diisopropylphenyl |
| CSP V | (R)-α-methylbenzyl |
| CSP VII | triphenylmethyl (trityl) |
| 9, 11-subst.-10, 11-dihydroquinidine carbamate CSPs | |
| CSP III | 3,5-dinitrophenyl |
| CSP V | (R)-α-methylbenzyl |

Dimeric DHC-based CSPs

| CSP | R₁ |
|---|---|
| 9, 11-subst.-10, 11-dihydroquinine carbanate CSPs | |
| CSP XIII | 1,6-hexamethylen-DHC |
| CSP XV | trans-1,4-cyclohexylen-DHC |
| CSP XVI | 1,3-phenylen-DHC |
| 9, 11-subst.-10, 11-dihydroquinidine carbamate CSPs | |
| CSP XIV | 1,6-hexamethylen-DHC |

CINCHONAN BASED CHIRAL SELECTORS FOR SEPARATION OF STEREOISOMERS

BACKGROUND

In nature a great variety of organic constituents are made up of chiral molecules with the emphasis to use the inherently stored stereochemical information within the molecules for a dedicated and most effective regulation of chemical processes. Enantiomers are chiral molecules which behave like non-superimposible mirror images of each other, whereby the configuration at the centers of chirality are determined by priority rules. In a non-chiral environment or without any chiral auxiliaries enantiomers are identical from a physicochemical point of view. However, if enantiomers get in close contact with a chiral auxiliary thus forming molecule associates, one results diastereoisomers of which the physical properties are different. This general concept can be used advantageously to distinguish between enantiomers and to set up strategies to synthesize and/or to separate enantiomers and to isolate the individual stereoisomers in enantiomerically pure form.

A one-to-one mixture of the enantiomers of a particular compound is called racemate or racemic mixture. In order to resolve this mixture to generate the two individual enantiomers two promising concepts can be followed. One relies on the preferential chemical modification or reaction of one of the enantiomers using a stereoselective reaction scheme implementing (bio)catalytic synthesis routes and synthesis concepts with chiral induction, respectively. This strategy involves stereoselective molecular recognition processes and the chiral auxiliary resigns in the chiral catalysts or chiral reactands. In the last years great progress has been made in this field to synthesize enantiomerically pure compounds (EPCs) with high chemical and stereochemical yield. However, it is still quite rare to reach EPCs with enantiomeric excess (ee) values of 99% or greater, which implies that one still may need additional methods and processes for the enantiopurification to the desired ee values.

This second strategy to observe EPCs relies on separation processes involving chiral auxiliaries, selectors (SOs) with which the individual enantiomers within their mixture are forming quasi diastereomeric transient molecule complexes or molecule associates of different physicochemical properties, including association and/or dissociation constants. The more these types of diastereomers differ in their energy content (expressed as $\Delta\Delta G$ values) the more efficient a stereoselective separation process may be established. The intermolecular binding forces active in the course of forming the diastereomeric selector (SO)—selectand (SA) molecule associates span from electrostatic interactions, including dipole-dipole interactions to hydrogen bonding, $\pi$—$\pi$ type interactions to van der Waal type interactions in conjunction with steric parameters which may be described as steric attraction (fit) or repulsion (non-fit). Consequently and as a result of this great variability of stereodiscriminatively active SO-SA interactions the chemical constitution of selector compounds is very high. However, a successful concept relies on complementary interactions between SO and SA, which implies that for given selectands with their chemical structure optimal selectors may exist, or vice versa, with respect to the development of efficient separation methods to generate EPCs. From a general and methodological point of view fractionated crystallization methods, liquid-liquid and liquid-solid type extraction methods are most promising, including chromatographic and membrane type separation methods. Recent reviews describing the various techniques in the field are given by [S. Allenmark (Ed.), *Chromatographic Enantioseparation: Methods and Applications*, Wiley, New York, (1988); G. Subramanian (Ed.), *A Practical Approach to Chiral Separations by Liquid Chromatography*, VCH, Weinheim, (1994); J. Jacques, A. Collet, S. H. Wilen, *Enantiomers, Racemates, and Resolutions*, Krieger Publ. Comp., (1994);].

To summarize, the chemical structure of a chiral selector described by its overall spatial size and (supra)molecular structure, by the number of stereogenic centers and their absolute configurations, by the nature and size of the various substituents of the stereogenic centers and the conformation of the solvated compound, and by the number and types of functional groups within the compound will eventually define as a sum parameter the interaction domains of a selector compound. The selectand molecules, respectively each individual enantiomer of a pair of enantiomers, may get selectively attracted or even repulsed by the multivariate interaction sites within the SO and SA moiety, whereby the magnitude of the differences can vary from very small to great.

Within the group of prominent chiral auxiliaries and selectors to be used for enantioseparations the cinchona alkaloids proved their potential which goes back to the beginnings of stereochemistry and of chiral resolutions. Since then these compounds found a number of applications as resolving agents for the fractionated crystallization of chiral acids as diastereomeric salts [P. Newman, *Optical Resolution Procedures for Chemical Compounds*, Volume 2, Part I and II, Optical Resolution Information Center, Manhattan College, Riverdale, N.Y. 10471, 1981]. Among the most often used cinchonan based resolving agents are to be mentioned the naturally occurring bases quinine, quinidine, cinchonine and cinchonidine as well as their synthetic derivatives, the respective 1-methyl or 1-benzyl quaternized salts which all leave the hydroxyl group at the chiral $C_9$ carbon non-substituted. However, it should be mentioned at this point that quinine and quinidine as well as their ester derivatives are known to be chemically relatively labile [Y. Yanuka et al., *Tetrahedron*, 43 (1987) 911] which prevented them from their more frequent use as chiral auxiliaries in crystallization protocols. Cinchona alkaloids have also been employed successfully for diverse stereodiscriminating techniques in the field of liquid-phase separations. In this context one of the most popular concepts for the discrimination of enantiomers has become the direct HPLC enantioseparation method with a chiral additive to the mobile phase together with an achiral stationary phase (CMP) or with an achiral mobile phase together with a chiral stationary phase (CSP). Also cinchona-alkaloids have been utilized in accordance with these two concepts, but so far with minor success. In all cases reported in literature, the secondary hydroxyl group grafted to the $C_9$ carbon was unsubstituted or was esterified (acetylated, p-chlorobenzoylated). Such chiral selectors were either added to the mobile phase [A. Karlsson et al., *Chirality*, 4 (1992) 323] or immobilized onto silica [P. Salvadori et al., *Tetrahedron*, 43 (1987) 4969; *Chirality*, 4 (1992) 43; P. N. Nesterenko et al., *J. Chromatogr. A*, 667 (1994) 19]. As stated above these selectors suffered also from chemical instability which restricted their applicability. Very recently, native quinine was employed also as an additive to the running buffer in non-aqueous capillary zone electrophoresis and used as chiral discrimination auxiliary or selector for the separation of the enantiomers of 3,5-dinitrobenzoylated amino acids and other chiral acids [A. M. Stalcup et al., *J. Microcolumn Separations*, 8(2), (1996) 145].

Besides in the stereoselective separation methods, cinchona alkaloids and derivatives thereof, respectively, play an important role also in the field of stereoselective synthesis as homogeneous and heterogenous chiral auxiliaries or ligands in asymmetric catalysis. The most effective and important ones are cited in [H. Brunner et al., *Handbook of Enantioselective Catalysis*, Vol. I and II, VCH, Weinheim, New York, 1993; H.-U. Blaser, *Chem. Rev.*, 92 (1992) 935]. Mostly, the hydroxyl group of the chiral $C_9$ carbon remained unsubstituted, since the hydroxyl group is presumed to play a key role in the diastereomeric complex formation of the transition states. On the other side, from the group of Sharpless we know that O-derivatized cinchona alkaloids also act as excellent chiral ligands in asymmetric syntheses, e.g., in the osmium-catalyzed asymmetric dihydroxylation or aminohydroxylation of olefins [Sharpless et al., WO 92/20677]. This group found that particularly ether type derivatives of the alkaloids, especially of dihydroquinine and dihydroquinidine, gave the highest optical yields and reaction rates in the course of osmium catalyzed addition reactions of olefinic compounds [H. C. Kolb et al., *J. Am. Chem. Soc.*, 116 (1994) 12783. Other derivatives tested concerned ester analogues of the dihydroalkaloids (e.g. p-chlorobenzoyl esters) but also some carbamate derivatives, namely N, N-dimethyl, N-methyl-N-phenyl, N-phenyl and N, N-diphenyl carbamates of cinchona alkaloids have been described [Sharpless et al., WO 92/20677]. However, these carbamates of dihydroquinidine (the 11 position remained unsubstituted; the vinyl group of the alkaloid had to be hydrogenated to be a useful catalyst for the dihydroxylation of olefins) employed as chiral auxiliaries in stereoselective catalysis reactions did express relatively poor chiral induction compared to the ether derivatives. The ester and amide group did obviously not support a pronounced stereocontrolled recognition process in the course of catalytic asymmetric dihydroxylation of olefines. However, for stereodiscrimination processes with respect to separation technologies cinchona alkaloid carbamates, ureas, amides, etc., have not been utilized and described, but these cinchona alkaloid derivatives may provide special features by manipulating and optimizing the substitution pattern and thus also improving considerably the chemical and stereochemical stability of cinchona alkaloids.

In this context and in order to expand the spectrum of cinchona based selectors but with positionally switched hydrogen donor-acceptor functionalities close to the chiral $C_9$ position 9-amino (9-deoxy) cinchona derivatives have also been made subject of the present invention. Hence, only little interest has been directed towards the diamines derived from cinchona alkaloids by replacing the 9-hydroxyl function by an amino group. The first synthesis described by [S. Fränkel, C. Tritt, M. Mehrer and M. Herschman, *Chem.Ber.* 58, 549 (1925)] involves treatment of potassium phthalimide or sodium benzenesulfonamide with quinine chloride at elevated temperatures in vacuum to give in the first step the corresponding phthalimide and benzenesulfonamide which were characterized as their picrates. Subsequent acidic hydrolysis of the amide gave the corresponding amine which was converted to sulfate and picrate. However, since the synthetic strategies employed involve conditions which are known to lead to isomerization at $C_9$ or re-arrangement of the quinuclidine ring [P. Rabe, *Liebigs Ann. Chem*, 561, 132 (1948)] the stereochemistry of the amine and amides, respectively, reported by Fränkel et al. is difficult to establish. [G. R. Pettit and S. K. Gupta, *J.Chem. Soc.* ( C ) 1208 (1968)] reported a different approach based on LiAlH4 reduction of oximes of quinidinone and cinchonidinone Most recently, an efficient synthesis of 9-amino-(9-deoxy)-cinchona alkaloids based on Mitsunobu chemistry has been developed and the stereochemistry of the products established by X-ray crystallography [H. Brunner, J. Bügler and B. Nuber, *Tetrahedron: Asymmetry*, Vol.6, 7, 1699 (1995)]. However, up to date no application of these cinchona alkaloids derived diamines in chiral discrimination using chromatographic methods or membrane technologies or solid-phase extraction methods or crystallographic methods has been described.

BRIEF DESCRIPTION OF THE PRESENT INVENTION

Subject of the present invention is the synthesis of a variety of novel 9-substituted cinchonan and 9,11-substituted 10,11-dihydrocinchonan derivatives, respectively, which possess hydrogen donor-acceptor groups as part of an amide structure element or partial structure element, respectively, thus providing simultaneously active and ambivalent hydrogen bonding areas via hydrogen donating accepting groups which are useful in the methods and processes of the present invention related to enantioseparation by liquid-liquid, liquid-solid and membrane technologies and fractionated crystallization. The involvement of the strong amino group of $N_1$ in a co-operative way with the additional functional groups of the present invented selectors is of prime importance and is of profound difference to the hence described enantioseparation methods.

In one embodiment of the present invention the chiral selector is immobilized onto support material or incorporated within a polymer leading to 9,11-disubstituted 10,11-dihydrocinchonan derivatives. These materials are useful for stereoselective liquid-solid phase extraction and separation technologies. A particular advantage of the present invented selectors is also their excellent chemical and stereochemical stability making them recyclable many times in the course of enantioseparations by liquid-liquid extraction methods, by fractionated crystallization methods, and in the course of liquid-solid extractions.

BRIEF DESCRIPTION OF THE DRAWINGS

FIG. 10 depicts the chemical structures of various carbamate type CSPs based on the 9,11-subst.-10,11-dihydrocinchonan skeleton.

DETAILED DESCRIPTION OF THE PRESENT INVENTION

Figure 1:
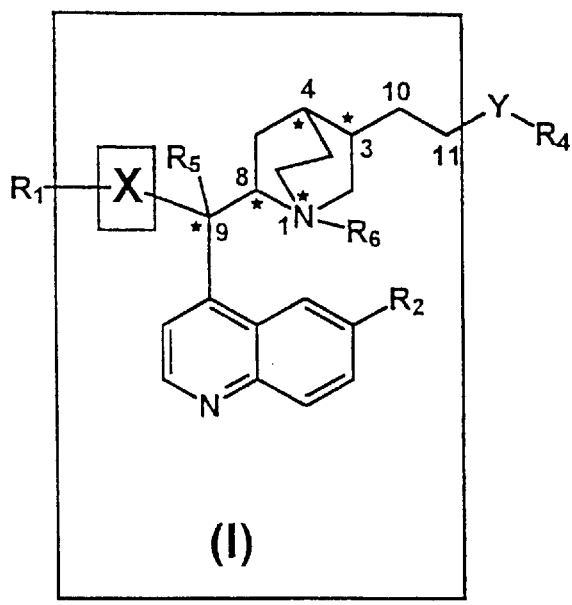
FIG. 1 represents the general structure and skeleton of the present invented 9,11-substituted-10,11-dihydrocinchonan derivatives derived from 9-substituted-cinchonan-precursors.
Figure 1:
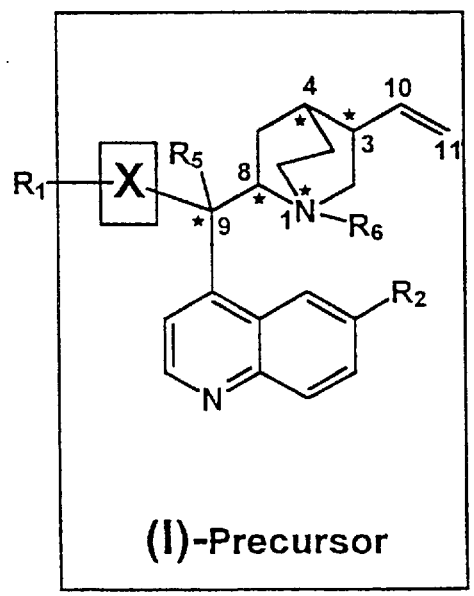
Figure 2:
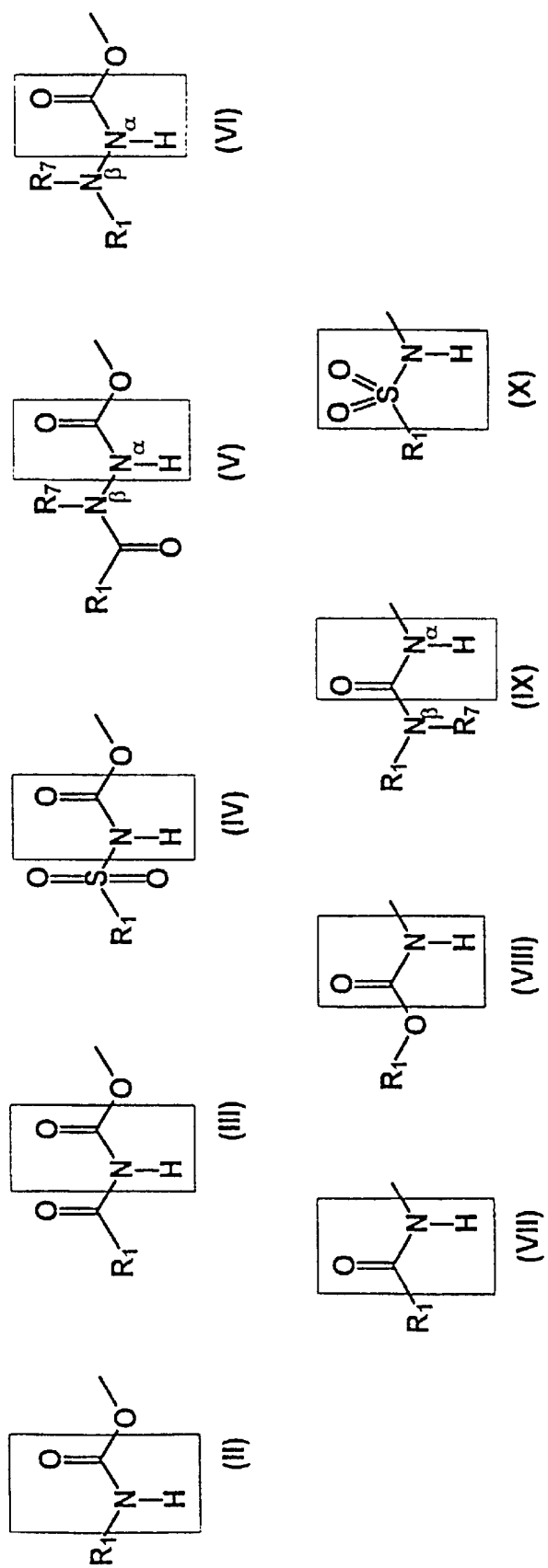
FIG. 2 is a schematic representation of functional groups with —NHCO- or —NHSO$_2$-structural elements which are key elements of the present invented compounds derived from cinchona alkaloids.

The separation of enantiomers has been the subject of much research for many years and the spectrum of differently substituted chiral selectors examined is quite large (G. Subramanian (Ed.), *A Practical Approach to Chiral Separations by Liquid Chromatography*, VCH, Weinheim, 1994]. However, little research has been directed towards the investigation of chiral selectors with structural elements composed of chargeable (ionizable) groups, as they are strong bases or acids, together with hydrogen donor acceptor functionalities and π-π-interaction binding groups thus providing a well balanced spectrum of multifunctional and potentially binding areas within a selector moiety with at least in some parts complementary structured selectand molecules. In order to make this concept successfully working the thus modulated selector compounds need also to have considerable conformational rigidity paired with good chemical and stereochemical stability. Based on all these considerations we found that cinchona alkaloids can be used advantageously as chiral templates to be modified by dedicated synthesis strategies to improve the properties of this type of alkaloids with respect to highly selective and useful applications in the various fields of enantioseparations. Accordingly the present invention relates to compounds of the general formula (I) and of (I)-precursors (see FIG. 1) with the 9,11-substituted-10,11-dihydro-cinchonan skeleton (9,11-Subst.-DHC skeleton), including the 9-substituted cinchonan precursors (9-Subst.-C) thereof, and their various stereoisomers related to the configurations of the centers of chirality marked with *, wherein X is a substituent of any one of the functional groups (II) to (X) (presented in FIG. 2) and wherein Y is a thio group (thioether; S), a sulfinyl group (sulfoxide; SO) such introducing a new chiral center marked with *, or a sulfonyl group (sulfon; $SO_2$), and wherein the groups $R_1$ to $R_7$ are the following:

$R_1$ is hydrogen atom, an optionally substituted aliphatic linear or branched, non-chiral or chiral $C_1$–$C_{36}$ group, an optionally substituted non-chiral or chiral alicyclic or heteroalicyclic group, an optionally substituted aromatic or heteroaromatic group, an optionally substituted non-chiral or chiral arylalkyl group, a trialkylsilyl group, an optionally substituted cinchonanyl group, or a group derived thereof.

$R_2$ is a hydrogen atom, a hydroxy group or an alkoxy group of the general formula—$OR_3$ wherein $R_3$ is an aliphatic $C_1$–$C_{18}$ group, or an alicyclic group.

$R_4$ is a hydrogen atom, an optionally substituted aliphatic linear or branched, chiral or non-chiral $C_1$–$C_{36}$ group, an optionally substituted non-chiral or chiral alicyclic or heteroalicyclic group, an optionally substituted aromatic or heteroaromatic group, or an optionally substituted non-chiral or chiral arylalkyl group.

$R_6$ is a hydrogen atom, an optionally substituted alkyl or aryl group.

$R_6$ is missing thus signifying the free base, or a hydrogen atom in the case of ammonium salts, an optionally substituted aliphatic linear or branched, non-chiral or chiral $C_1$–$C_{18}$ group, an optionally substituted non-chiral or chiral alicyclic group, or an optionally substituted non-chiral or chiral arylalkyl group.

$R_7$ is a hydrogen atom, an optionally substituted alkyl or aryl group.

$R_1$, $R_4$, $R_6$ may be any one of the prior mentioned groups with acidic functions (carboxylic, sulfonic, sulfinic, phosphinic, phosphonic, phosphoric group) thus obtaining amphoteric compounds.

$R_1$, $R_4$ may be any one of the prior mentioned groups with an appropriate function with which the 9,11-Subst.-DHC derivative is immobilized onto silica.

$R_1$, $R_4$, $R_6$ may be any one of the prior mentioned groups with an appropriate function with which the 9,11-Subst.-DHC derivative is dimerized, trimerized, tetramerized, oligomerized, polymerized or copolymerized.

Figure 3:
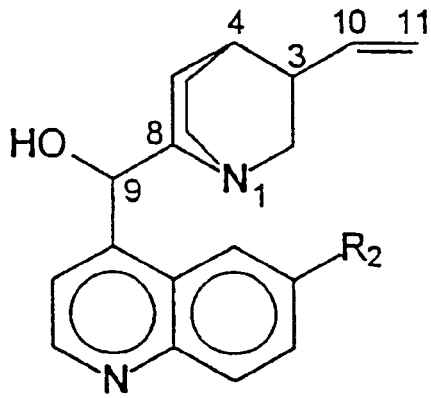
FIG. 3 represents the structure and stereochemistry of the native cinchona alkaloids which have been employed as starting material for the synthesis of the present invented dihydrocinchonan and cinchonan derivatives. Also the corresponding 10,11-dihydroalkaloids are known and can be found in the native alkaloid mixture isolated from cinchona succiruba bark; for obvious reasons they cannot be used as starting material or precursors for our synthesis concept due to their inability to generate 11-substituted dihydrocinchonan derivatives.
Figure 4:
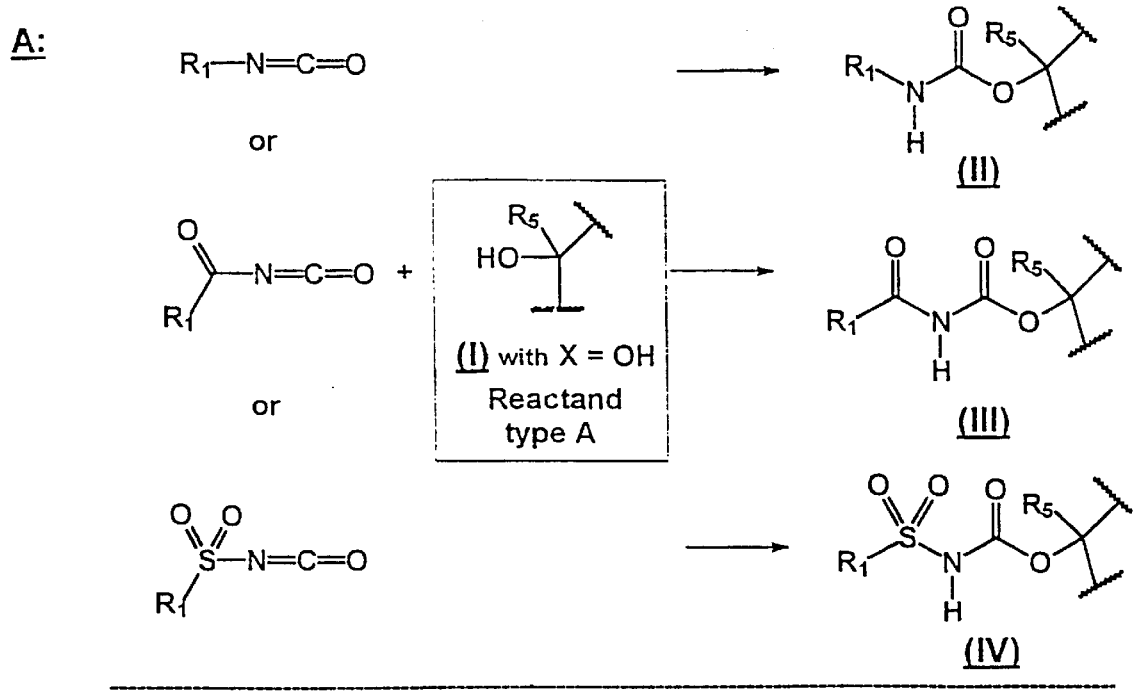
FIG. 4 shows the general reaction scheme for the preparation of substituted dihydrocinchonan and substituted cinchonan type selectors which contain the diverse structural elements (II) to (IV) and (VII) to (X). Reactand type A represents (optionally substituted) $C_9$-hydroxy-10,11-dihydrocinchonan and $C_9$-hydroxy-cinchonan skeleton, respectively. Reactand type B represents (optionally substituted) $C_9$-amino-10,11-dihydrocinchonan and $C_9$-amino-cinchonan skeleton, respectively.
Figure 4:
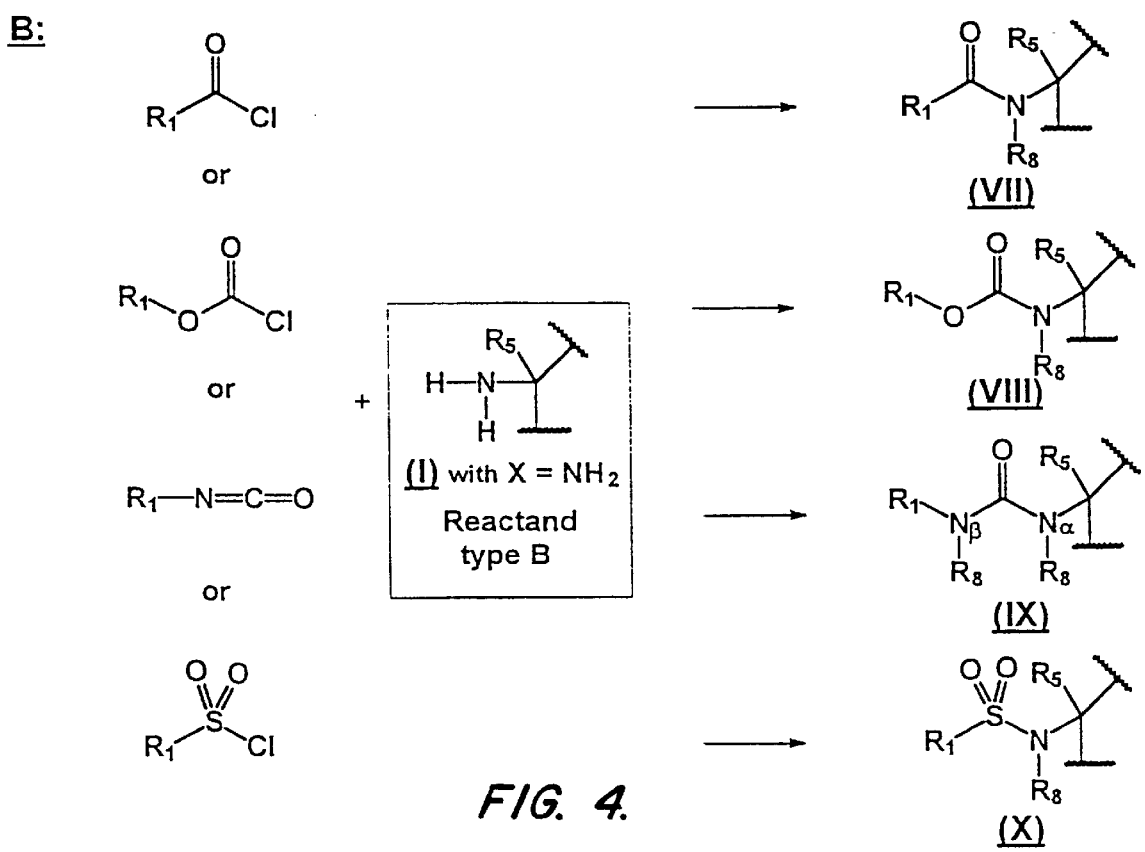
Figure 5:
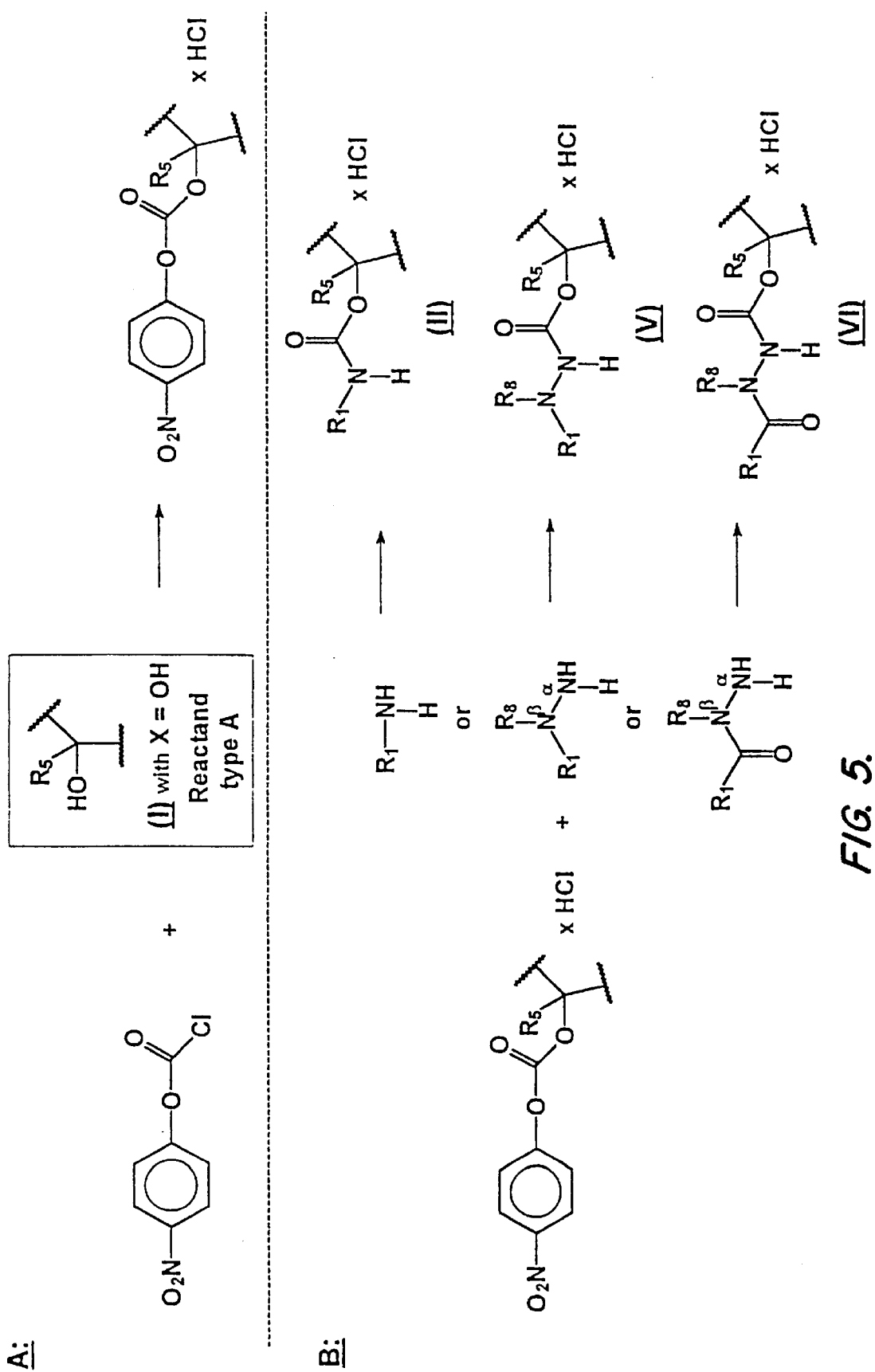
FIG. 5 shows the reaction scheme for the preparation of substituted dihydrocinchonan and substituted cinchonan type selectors and which contain the diverse structural elements (II), (V) and (VI) implementing an active ester method for the preparation of compounds with an amide partial structure.

These new compounds are derived from cinchonaalkaloids as depicted in FIG. 3, and are obtained by their subsequent modification and their chiral and/or chemical transformation. The most common compounds of this alkaloid family are the native alkaloids quinine, quinidine, cinchonine and cinchonidine as well as their respective epi-congeners, and of some of them also the 10,11dihydro compounds are known. The five stereogenic centers within the semi-rigid framework of the cinchonan skeleton and the particular conformation of the so-called chiral host or chiral selector (SO) compounds provide an excellent basis for effective chiral recognition of guest molecules (ligands), which are in stereodiscrimination processes also termed chiral selectands (SAs). The effective chiral information built in into the selector compounds becomes, however, especially stereodirecting in combination with appropriate functionalities. Thus, an additional functional group fitting to the structures (II) to (X) is introduced into the cinchonan skeleton via the otherwise non-substituted secondary alcoholic group at the carbon $C_9$ of the cinchonan based alkaloids or via the amino group of 9-amino cinchonan that is accessible by chemical modification of the native alkaloids. All these introduced structural elements of (II) to (X) have in common a hydrogen donor acceptor function which turned out to be of major relevance particularly in conjunction with the strong amino group steming from the quinuclidine group. Surprisingly, it has been found that these functional groups favour stereodiscrimination due to the additional sites for specific intermolecular interactions by directed hydrogen bonding and/or dipole-dipole interaction with complementary functional groups in the ligand molecule (selectand, SA), and thus seems to be of essential importance for the unexpectedly high enantioselectivity of the present investigated chiral selectors. The carbonyl (—CO—) partial structure may serve as hydrogen acceptor group and the amide (—NH—) structural element (if unsubstituted) as hydrogen donor group besides the ability of amide groups to serve also as an electrostatic dipole accessible for dipole-dipole stacking (interaction); via the moieties $R_1$ to $R_7$ additional steric and/or $\pi$-$\pi$-interaction sites as well as other interaction sites have been introduced, which can further increase stereoselectivity of the chiral selectors. The surprisingly enhanced stereodiscrimination capability of 9,11-subst.-DHC and 9-subst.-C derivatives, in comparison to the non-modified alkaloids and to compounds with an ester or ether derivatized $C_9$-hydroxy group, may also be attributed to their more restricted conformational flexibility compared to their unmodified and former mentioned congeners; however, the 9,11-subst.-DHC and 9-subst.-C derivatives still allow and favour a stereoselective "induced fit" in the ligand binding and SO-SA-binding process. These new structural elements and their favourable location at the stereogenic center at $C_9$ generate together with $C_8$ and $N_1$ and the functional and bulky substituents at these stereogenic centers and in combination with the substituents at $R_1$ and in some extent at $C_{11}$, a polarized "chiral pocket or cleft" which represents a dominant "active chiral recognition site" of the diverse chiral selectors. This new chiral recognition site of e.g. carbamate, urea, or amide derivatives is very much different from the chiral recognition site of the quinine (quinidine, etc,) derivatives with the unsubstituted secondary hydroxl group at $C_9$, that very unexpectedly even a reversal of the stereodirected binding strength and elution order of a given set of enantiomeric selectands, e.g. of 3,5-dinitrobenzoyl leucine, occurred although all stereogenic centers of the selectors, which are usually the prime determinants for binding and elution order, respectively, remained the same. These 9,11-subst.-10,11-DHC and the 9-subst.-C derivatives are conveniently accessible by common chemical reactions. DHC and C carbamates (II), (III) and (IV) are either obtained by reaction of the respective isocyanate with the secondary alcoholic group of the chiral carbon $C_9$ of the given cinchonan reactand (see FIG. 4, A) or via reaction of the 4-nitrophenyl carbonate of the respective DHC and C skeleton, respectively, (activated ester derivative; see FIG. 5, A) with the respective amino compound (see FIG. 5, B). The DHC and C ureas (IX) are obtained by reaction of the given 9-amino cinchonan derivative with the respective isocyanate, DHC and C amides (VII) by reaction with the respective carboxylic acid chlorides, DHC and C carbamates (VIII) by reaction with chloroformates, and DHC and C sulfonamides (X) by reaction with sulfonylchlorides. DHC and C derivatives with hydrazine-partial structure (V) and (VI) are also obtained via the activated ester compound (see FIGS. 5, A and B). Via the several substituents spanning from $R_1$ to $R_7$ highly directive additional and functional groups are introduced to modify the selectors to distinct properties:

A chiral sulfoxide function at $C_{11}$ surprisingly further increase the stereodiscrimination capability of the 9,11-subst.-DHC derivatives.

Lipophilic groups via $R_4$ but also via other substituents increase the overall solubility of the derivatives in organic solvents to be used in liquid-liquid extraction and related techniques including liquid supported membrane techniques, but without diminishing stereoselectivity.

The introduction of an anchor group makes possible the immobilization onto silica (porous and non-porous) to yield chiral stationary phases (CSPs) for liquid chromatography (especially for analytical as well as preparative LC) and electrochromatography, but without effecting the high stereoselectivity significantly.

The introduction of polymerizable groups enables the preparation of chiral polymers or imprinted chiral polymers including chiral bead type polymers, but also useful for the preparation of chiral polymer coated silica.

Via $R_6$ substituents are introduced to yield quaternized salts which may serve as strong anion-pairing and/or anion exchange type selectors.

The introduction of acidic and chargeable functions via $R_1$, $R_4$, $R_6$ yield amphoteric selectors for ion pairing with complementary charged chiral acids, chiral bases and chiral amphoteric compounds thus making the chiral selectors even more broadly applicable.

Via $R_6$ substituents are introduced to trigger the conformational rigidity of DHC and C derivatives.

Via $R_2$ substituents the electron density of the quinoline ring can be changed and if $R_2$ is a hydroxyl group it can be used to prepare e.g. chiral azo dyes or to introduce lipophilic or charged groups. All these groups are introduced employing common chemical reactions of organic chemistry. These modifications may be performed either before or subsequent to the major or primary X-modification step. Inherently connected to the dedicated modification of the chiral selectors based on cinchona alkaloids is the use and/or the application of these compounds as chiral selectors in stereoisomer recognition and stereodiscrimination methods:

in liquid-phase separation systems: as chiral stationary phases (CSPs) or as chiral additives to the mobile phase (CMP) in liquid chromatography, capillary electrophoretic or electrochromatographic enantiomer and stereoisomer separation, as chiral carriers in liquid-liquid extraction, in liquid supported membrane technologies, countercurrent like extraction, and as chiral polymeric material to be used for fixed bed membrane technology, for liquid-solid extraction processes, and for rescue type separation technologies.

for fractionated crystallization: as chiral resolving agents (chiral auxiliary with basic or amphoteric character) for the resolution by crystallization of stereoisomers of chiral bases, chiral acids and chiral amphoteric compounds via diastereomeric salt formations. These methods include processes for the enantioseparation of chiral neutral compounds with polar groups, chiral addic compounds, chiral basic and amphoteric compounds wherein the chiral acidic compounds are selected from the group consisting of carboxylic acids, sulfonic acids, phosphoric acids, N-protected $\alpha$-, $\beta$-, or $\gamma$-amino acids, (hetero)arylalkyl carboxylic acids, (hetero)aryloxy carboxylic acids, (hetero)arylthio carboxylic acids, substituted alicyclic carboxylic acids, $\alpha$-, or $\beta$-alkyl alkanoic acids, (substituted) $\alpha$-allyl, or $\alpha$-benzyl acetic acids, free $\alpha$-, $\beta$-, or $\gamma$-amino acids, free peptides, N-derivatized peptides, NH-acidic benzimidazolyl sulfoxides, OH acidic coumarins, acidic compounds with imide structures, and acidic atropisomeric biphenyls or binaphthyls and wherein the basic and amphoteric compounds are Ca-antagonists selected from the group consisting of verapamil, gallopamil, and 1,4-dihydropyridine-3,5-dicarboxylic acid mono methyl esters.

The invention will be illustrated by the following examples:

EXAMPLE 1

Synthesis of Chiral Stationary Phase CSP I Based on O-(t.-butylcarbamoyl)-quinine as chiral selector a.) General protocol for the synthesis of precursors with carbamate structure prepared via isocyanate reaction of the $C_9$ hydroxyl group exemplified by the synthesis of the O-(t.-Butylcarbamoyl)-quinine selector:

3.0 g of quinine (as free base) were dissolved in dry toluene. 1.2 ml of t.-butyl isocyanate and 1 drop of dibutyl tin dilaurate as catalyst were added. The mixture was refluxed for 4 hours, the solvent evaporated and the remaining raw material washed with n-hexane. The white solid was crystallized with cyclohexane resulting O-(t.-butylcarbamoyl)-quinine in 70% yield.

Physical properties: m.p.: 122° C.; $[\alpha]^{23}_{Na589}$=−10.9°, $[\alpha]^{23}_{Hg546}$=−15.8° (c=1.01; MeOH); IR (KBr): 1718, 1622, 1593, 1532, 1508, 1267, 1035 cm$^{-1}$. $^1$H-NMR (200 MHz, dMeOD): 8.68 (d, 1H), 7.95 (d, 1H), 7.57 (m, 2H), 7.45 (dd, 1H), 6.50 (d, 1H), 5.80 (m, 1H), 4.9–5.1 (m, 2H), 4.01 (s, 3H), 3.2–3.4 (m, 3H), 3.0–3.3 (m, 1H), 2.5–2.8 (m, 2H), 2.25–2.45 (m, 1H), 1.7–2.0 (m, 3H), 1.5–1.70 (m, 2H), 1.2–1.4 (s, 9H) ppm.

b.) Grafting of O-(t.-butylcarbamoyl)-quinine to porous 3-mercaptopropyl silanized silica:

3.0 g of porous 3-mercaptopropyl silanized silica (4.58% C, 1.12% H) were suspended in chloroform. After addition of 2 g of O-(t.-butylcarbamoyl)-quinine and 200 mg of the radical initiator azo-α,α'-bis-isobutyronitrile (AlBN) the suspension was refluxed 15 hours flushing with a soft stream of nitrogen. The modified silica was sedimented, the solvent removed and the chiral sorbent washed with chloroform, methanol and petrolether. The dry modified silica was subjected to elemental analysis.

CHN-analysis: 12.7% C, 1.89% H, 1.25% N. This corresponds to a calculated selector coverage of about 0.27 mmol/g silica.

c.) End-capping of the modified chiral sorbent:

3.0 g of the modified silica, 2.0 ml 1-hexene and 200 mg of AlBN were refluxed in chloroform for 15 hours under nitrogen. The modified silica was washed as described above, dried and sieved.

CHN-analysis: 13.27% C, 1.97% H, 1.25% N. Thus, about 80 μmol thiol groups per gram silica were modified with lipophilic hexyl groups.

d.) Finally, 3 g of the chiral sorbent based on O-(t.-butylcarbamoyl)-quinine as selector were obtained and packed into a stainless-steel HPLC column of the dimension 150×4.0 mm I.D. by a conventional slurry packing method (Also all other porous CSPs have been packed by this procedure into columns of the same dimensions). After preconditioning with the appropriate mobile phase these HPLC columns were ready to be used for direct enantioseparation according to liquid-solid separation techniques.

EXAMPLE 2

Synthesis of Dimeric CSP XVI Based on 1,3-phenylene-bis-[O-(carbamoyl)-quinine] as chiral selector a.) Synthesis of 1,3-phenylen-bis-[O-(carbamoyl) quinine]

3.0 g of quinine (as free base) were dissolved in dry toluene. An 0.45 molar amount of 1,3-phenylene diisocyanate and 1 drop of dibutyl tin dilaurate as catalyst were added. The mixture was refluxed for 4 hours, the solvent evaporated and the remaining raw material washed with dry diethylether. The white solid was purified by flash cromatography with silica gel and yielded 2.4 g of the pure product.

Physical properties: m.p.: 146–152° C.; $[\alpha]^{23}_{Na589}$=+85°, $[\alpha]^{23}_{Hg546}$=+102° (c=0.99; MeOH); IR (KBr): 3431, 2932, 2865, 1729, 1621, 1545, 1511, 1495, 1475, 1456, 1433, 1307, 1230, 1190, 1087, 1045 cm$^{-1}$. $^1$H-NMR (200 MHz, dMeOD): 8.65 (d, 2H), 7.98 (d, 2H), 7.78 (s, 1H), 7.4–7.6 (m, 6H), 7.0–7.2 (m, 3H), 6.60 (d, 2H), 5.7–5.9 (m, 2H), 4.9–5.1 (dd, 4H), 4.00 (s, 6H), 3.95 (d, 1H), 3.5–3.7 (m, 2H), 3.0–3.4 (m, 4H), 2.6–2.9 (m, 4H), 2.3–2.5 (m, 2H), 1.5–2.0 (m, 10H) ppm.

b.) Grafting of 1,3-phenylene-bis-[O-(carbamoyl)-quinine] to 3-mercaptopropyl silanized silica:

3.0 g of 3-mercaptopropyl silanized silica (4.58% C, 1.12% H) were suspended in chloroform. After addition of 2 g 1,3-phenylene-bis-[O-(carbamoyl)-quinine] and 200 mg of the radical initiator AlBN the suspension was refluxed 15 hours flushing with a soft stream of nitrogen. The modified silica was sedimented, the solvent removed and the chiral sorbent washed with chloroform, methanol and petrolether. The dried modified silica was subjected to elemental analysis. CHN-analysis: 14.39% C, 1.91% H, 1.57% N. This corresponds to a calculated selector coverage of about 0.17 mmol/g silica.

c.) End-capping of the modified chiral sorbent: as described in example 1, c.)

d.) Finally, 3 g of the chiral sorbent based on 1,3-phenylene-bis-[O-(carbamoyl)-quinine] as chiral selector were obtained and packed into a stainless-steel HPLC column of the dimension 150×4.0 mm I.D. by a conventional slurry packing method.

EXAMPLE 3

Syntheses of 9-amino-(9-deoxy)-epiquinine derived precursors and of CSP XII a) 9-(tert.-butoxycarbonyl)-9-amino-(9-deoxy)-epiquinine A solution of 375 mg crude 9-amino-(9-deoxy)-epiquinine (prepared according to: H. Brunner et al., Tetrahedron, Asymmetry, Vol.6, 7, 1699 (1955)), 1.00 mL triethylamine and 500 mg di-tert.-butyl-dicarbonate in 5 mL dichloromethane was allowed to stand at ambient temperature for 24 h. The reaction mixture was diluted with 50 ml dichloromethane and washed twice with 30 mL 1 N aqueous NaOH. The organic layer was dried (MgSO$_4$) and the solvent removed under reduced pressure. The residual oil was purified chromatographically on 20 g silica using ethyl acetate as eluent to give 350 mg (71%) of a colorless oil that solidifies on standing at ambient temperature.

m.p.: 82° C.

$[\alpha]_{Hg546}$=+5.8; $[\alpha]_{Hg436}$=+4.2, (c=0.9, MeOH);

IR (KBr): 3424, 2931, 1708 cm$^{-1}$;

$^1$H-NMR (400 MHz, DMSO-d): 8.71 (d, 1H), 7.94 (d, 1H), 7.73 (s, 1H), 7.47 (s, 1H), 7.41 (d, 1H), 5.86 (m, 1H), 5.22 (s, 1H), 5.20 (s, 1H), 4.95 (m, 2H), 3.94 (s, 3H), 3.24 (m, 1H), 3.15 (dd, 1H), 2.67 (m, 2H), 2.23 (m, 1H), 1.52 (m, 3H), 1.32 (s, 9H), 1.03 (m, 1H) and 0.78 ppm (m, 1H);

b) 9-(3,5-dinitrobenzamido)-9-deoxy-epiquinine

To a solution of 600 mg crude 9-amino-(9-deoxy)-epiquinine in 20 mL dry dichloromethane was added a solution of 600 mg 3,5-dinitrobenzoyl chloride in 5 ml dry dichloromethane dropwise at ambient temperature with stirring. The reaction mixture was allowed to stand over night. The solid mass was suspended in 50 mL dichloromethane and 50 mL 1 N NaOH and stirred for 1 h. The organic layer was separated, dried (MgSO$_4$) and the solvent removed under reduced pressure gave 1.14 g of an orange oil. The crude material was purified chromatographically on 40 g silica using chloroform/triethylamine (3→5%) as eluent.

Removal of the solvent and drying in high vacuum gave 820 mg (83%) of a yellow foam.

m.p.: 138–140° C.

$[\alpha]_{Hg546}$=−71.7 (c=1.9, MeOH);

IR (KBr): 3423, 2935, 1664, 1625 cm$^{-1}$;

$^1$H-NMR (400 MHz,DMSO-d): 9.05 (s, 2H), 8.92 (s, 1H), 8.79 (d, 1H), 7.85 (s, 1H), 7.67 (d, 1H), 7.42 (d, 1H), 6.00 (m, 1H), 5.82 (s broad, 1H), 5.04 (m, 2H), 3.97 (s, 3H), 3.57 (dd, 1H), 3.17 (dd, 1H), 2.72 (dd, 1H), 2.63 (m, 1H), 2.27 (m, 1H), 1.55 (m, 4H) and 0.73 ppm (m, 1H);

c) 9-(p-toluoenesulfonamido)-9-deoxy-epiquinine

To a solution of 2.20 g crude 9-amino-(9-deoxy)-epiquinine and 2 ml triethylamine in 20 mL dichloromethane a solution of 2.12 g p-toluoenesulfonyl chloride in 5 ml dichloromethane was added dropwise with stirring at ambient temperature. The mixture was allowed to stand overnight. To the reaction mixture 50 ml 1N aqueous NaOH was added and the mixture was stirred for 1 h. The organic layer was separated, dried and the sovent removed under reduced pressure. The oily residue was purified chromatographically on 40 g silica with chloroform-triethylamine (20/1) to yield 2.15 g (65%) of a white foam.

m.p.: 82° C.

$[\alpha]_{Hg546}$=−20.0, $[\alpha]_{Hg436}$=−63.0; (c=1.5, MeOH);

IR(KBr): 3432, 2927, 1714, 1622, 1328 cm$^{-1}$ d) [(N$_\beta$-tert.-butyl)ureido]-9-deoxy-epiquinine A solution of 600 mg crude 9-amino-(9-deoxy)-epiquinine and 2.00 g tert.butyl isocyanate in 5 mL dioxane was kept in a sealed flask at 60° C. for 24 h. The solvent was removed under reduced pressure to give a yellowish oil that was purified chromatographically on 30 g silica using chloroform-triethylamine (3–5%) as eluent. Removal of the solvent and drying in high vacuum gave 655 mg (83%) of a white foam. An analytically pure sample was obtained by crystallization from ether/hexanes.

m.p.: 136° C.

$[\alpha]_{Hg546}$=−14.0; $[\alpha]_{Hg436}$=−43.7, (c=1.1, MeOH);

IR (KBr): 1676 cm$^{-1}$;

$^1$H-NMR (400 MHz,DMSO-d): 8.67 (d, 1H), 7.92 (d, 1H), 7.82 (s, 1H), 7.42 (m, 2H), 6.20 (d, 1H), 5.94 (s, 1H), 5.84 (m, 1H), 5.20 (s, 1H), 4.95 (m, 2H), 3.94 (s, 3H), 3.17 (m, 3H), 3.07 (q, 1H), 2.63 (m, 2H), 2.24 (m, 1H), 1.52 (m, 3H), 1.29 (q, 1H), 1.13 (s, 9H) and 0.78 ppm (m, 1H);

Immobilization of [(N$_\beta$-tert.butyl)ureido] 9-deoxy-epiquinine to mercaptopropyl modified silica (CSP XII)

600 mg of 9-amino-(9-deoxy)-epiquinine-tert.butylurea and 200 mg of 2,2'-azobis-(2-methylpropionitrile) was added to a suspension of 2.5 g mercaptopropyl-modified silica (5 μm) in 100 ml dry chloroform. The mixture was refuxed for 12 h under nitrogen with gentle stirring. Then 200 mg 2,2'-azobis-(2-methylpropionitrile) was added and heated for 10 h. The silica was allowed to settle and the turbid liquid removed by suction. Washing by resuspension and settling was repeated with chloroform (2×100 mL), methanol, ether and n-hexanes (2×50 mL). The material was dried at 60° C. in vacum to give 2.70 g modified silica. Elemental analysis gives 1.28% N, corresponding to a loading of 0.23 mmol selector/g modified silica.

EXAMPLE 4

Syntheses of Precursors Based on Epi-cinchona Alkaloids a) O-(t.Butylcarbamoyl)-epiquinidine 3.00 g Epiquinidine (prepared according to: J. Hiratake et al., J.Chem.Soc. Perkin Trans. 1, 1053 (1987)), 2.00 g tert.-butyl isocyanate and 1 drop dibutyltin dilaurate as catalyst was dissolved in 5 mL dry dioxane. The flask was sealed and kept at 60° C. for 6 d. The solvent was evaporated under reduced pressure and the oily residue purified chromatographically on 100 g silica with acetone as mobile phase to give 3.55 g (91%)of a white solid. An arialytically pure sample was obtained by crystallization from hexanes-ethyl acetate (5/1).

mp 128° C.

$[\alpha]_{Hg546}$=+133.1; $[\alpha]_{Hg436}$=+250.5, (c=1.50, MeOH);

IR (KBr): 1713 cm$^{-1}$;

$^1$H-NMR (400 MHz,CDCl$_3$): 8.76 (d, 1H), 8.03 (d, 1H), 7.56 (d, 1H), 7.39 (m, 2H), 6.25 (d, 1H), 5.90 (m, 1H), 5.13 (m, 2H), 4.88 (s, 1H), 4.00 (s, 3H), 3.26 (m, 1H), 3.00 (m, 4H), 2.29 (m, 1H), 1.64 (s, 1H), 1.53 (m, 2H), 1.28 (m, 10H) and 0.89 ppm (m, 1H);

b) O-(t.Butylcarbamoyl)-epiquinine

Prepared analogous to the procedure described for O-(t.butylcarbamoyl)-epiquinidine starting from 3.00 g epiquinine. After workup and purification 3.50 (89%) g of the corresponding carbamate was obtained.

m.p.: 164° C.

$[\alpha]_{Hg546}$=+12.3; $[\alpha]_{Hg436}$=+17.0, (c=0.6, MeOH);

IR (KBr): 1714 cm$^{-1}$;

$^1$H-NMR (400 MHz,CDCl$_3$): 8.77 (d, 1H), 8.04 (d, 1H), 7.62 (d, 1H), 7.37 (m, 2H), 6.23 (d, 1H), 5.77 (m, 1H), 4.97 (m, 2H), 4.88 (s, 1H), 3.97 (s, 3H), 3.35 (m, 3H), 2.75 (m, 2H), 2.28 (m, 1H), 2.08 (s, 1H), 1.63 (m, 3H), 1.37 (m, 1H), 1.23 (m, 9H) and 0.88 ppm (m, 1H);

EXAMPLE 5

Synthesis of a C$_9$-substituted precursor of a cinchona alkaloid

O-(tert.butylcarbamoyl)-9-methyl-quinidine 3.50 g 9-Methylquinidine dihydrate (prepared according to: R. B. Woodward et al., J.Am.Chem.Soc, Vol 67, 9, 1425 (1945)) was refluxed with 150 mL of toluene using a Dean-Stark trap to remove water azeotropically. After concentrating the solution down to 50 mL, 6.00 g tert.-butyl isocyanate and 1 drop of dibutyltin dilaurate as catalyst was added. The mixture was refluxed under nitrogen for 4 d. The reaction mixture was concentrated under reduced pressure. Purification of the residue via chromatography on 40 g silica with acetone gave 3.00 g (73%) of a white solid. An analytically pure sample was obtained by crystallization from ethyl acetate-hexanes.

m.p.: 162° C.

$[\alpha]_{Hg546}$=+23; $[\alpha]_{Hg436}$=+7.7, (c=1.25, MeOH);

IR (KBr): 1722 cm$^{-1}$;

EXAMPLE 6

Synthesis of CSP XIa based on O-(decylcarbamoyl)-1-methyl-quinidinium chloride as chiral selector (strong anion exchange type CSP-SAX type CSP)

Figure 6:
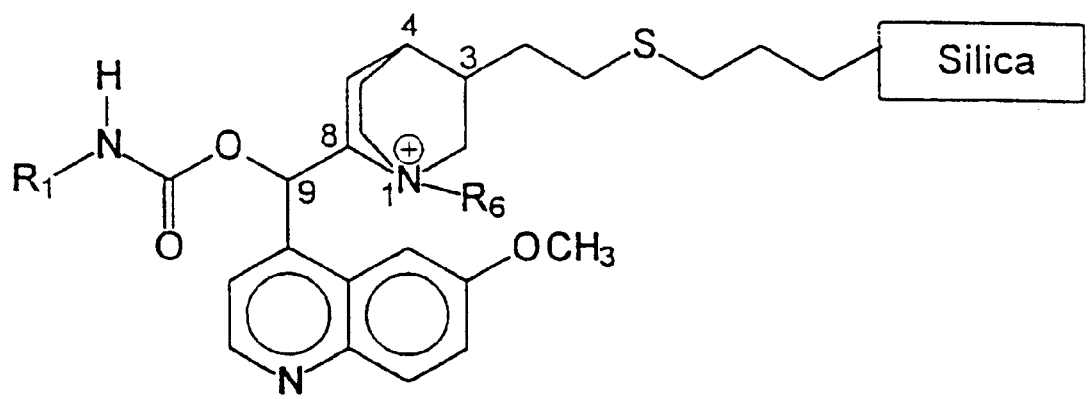
FIG. 6 depicts the chemical structures of CSP XIa and CSP XIb.

The chemical structure of CSP XIa is depicted in FIG. 6.

a.) Standard preparation protocol for the synthesis of quaternized precursors exemplified by the preparation of 1-methylquinidinium chloride (the quaternization may also be performed after the carbamate synthesis step in analogy): 5.0 g of quinidine (as free base) were dissolved in 10 ml of methanol and cooled to 0° C. An equimolar amount (0.99 ml) of methyl jodide was added. The mixture was allowed to stand overnight The precipitation was washed with a mixture of methanol/diethylether (1:3) and the product filtered and washed thoroughly with the prior mentioned solvents. The yellow material was crystallized with acetonitrile.

Yield: 3.26 g;

m.p.: 144° C.; $[\alpha]^{23}_{Na589}$=−138.2°, $[\alpha]^{23}_{Hg546}$=−171.7° (c=1.00; DMSO)

IR (KBr): 3200, 3078, 2992, 1620, 1588, 1510 cm$^{-1}$.

Before the product was bound to silica, the iodide was exchanged by chloride employing a strongly basic anion exchanger in the chloride-form (DOWEX 1×2; Fluka).

b.) Synthesis of O-(decylcarbamoyl)-1-methylquinidinium chloride 3 g of 1-methyl-quinidinium chloride were dissolved in chloroform and the mixture, after addition of 1 drop of dibutyl tin dilaurate, refluxed for 24 h with decyl isocyanate (obtained by Curtius-rearrangement out of undecanoic acid chloride and its azide, respectively). After evaporation of the chloroform the crude product was washed with diethylether to yield the pure product in 95% yield.

c.) Grafting of O-(decylcarbamoyl)-1-methyl-quinidinium chloride to porous 3-mercaptopropyl silanized silica as described in example 1, b.).

CHN-analysis: 9.31% C, 1.73% H, 0.50% N.

This corresponds to a calculated selector coverage of about 0.123 mmol/g silica.

d.) End-capping of the modified chiral sorbent as described in example 1, c.):

CHN-analysis: 10.56% C, 1.96% H, 0.49% N.

Thus, about 182 μmol remaining thiol groups per gram silica were modified with lipophilic hexyl groups.

e.) Finally, 3 g of the chiral sorbent were obtained and packed into a stainless-steel HPLC column of the dimension 125×4.0 mm I.D. by a conventional slurry packing method.

(CSP XIb—the chemical structure of CSP XIb is shown in FIG. 6—has been synthesized in analogy with the corresponding non-methylated or tertiary congener and the SO-coverage was about 0.154 mmol/g silica; weak anion exchange type CSP-WAX type CSP).

f.) Comparison of SAX and WAX type CSPs: Influence of mobile phase pH on retention and enantioselectivity of N-3,5-dinitrobenzoyl leucine enantiomers.

Figure 7:
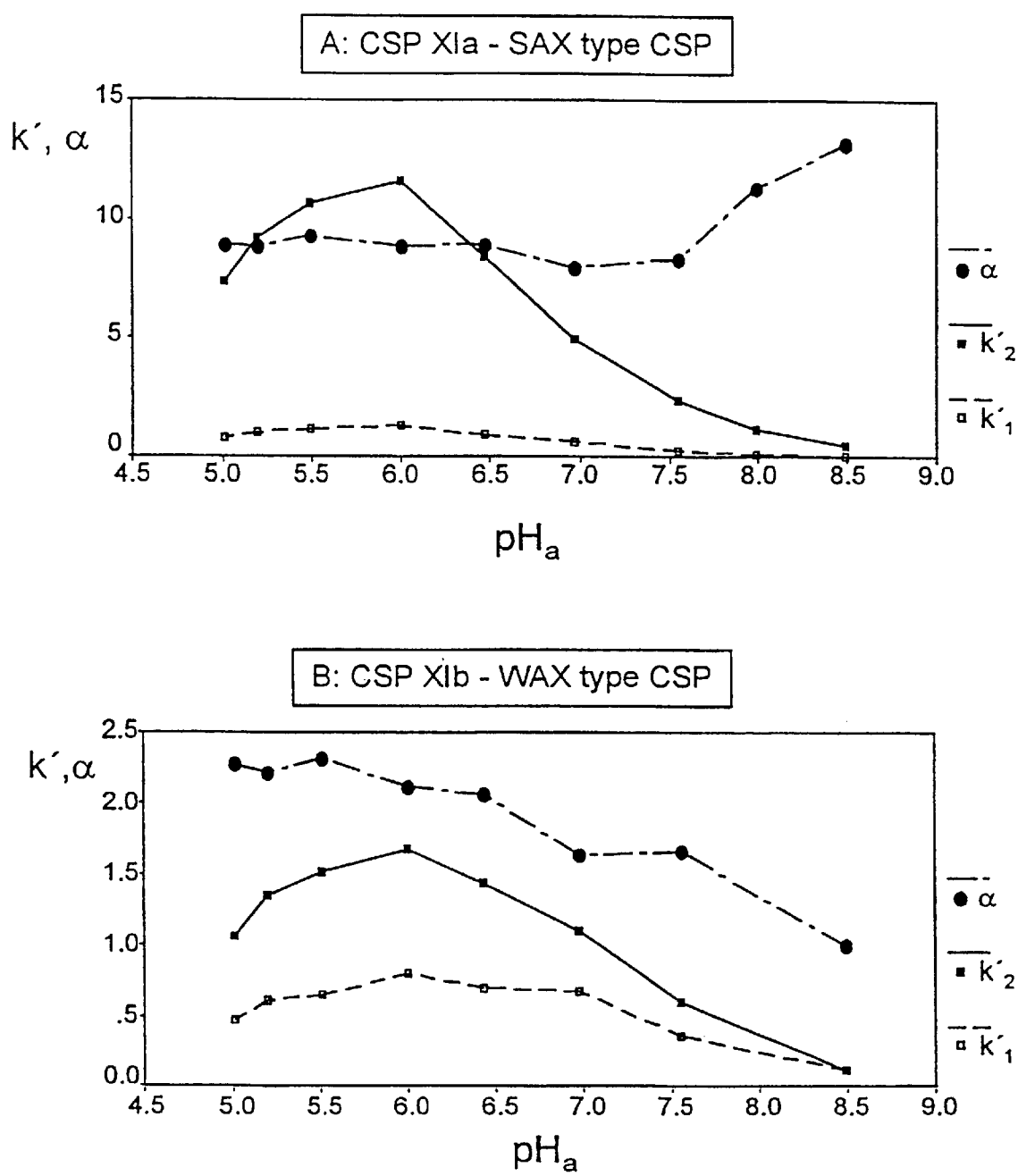
FIG. 7 shows the dependence of retention and enantioselectivity of N-3,5-dinitrobenzoyl leucine enantiomers on the pH of the mobile phase on a SAX versus a WAX type CSP based on carbamoylated quinidine selectors. (Chrom. cond.: 80% methanol/20% 0.1M ammonium acetate; T: 25° C.; Flow rate: 1 ml/min.; Det: UV 254 nm).

The pH$_a$-curves in FIG. 7 clearly demonstrate the pH-dependence of retention and enantioselectivity as typical for an anion exchange mechanism. WAX type CSPs exert their full ion exchange capacity in the weak acidic medium (pHa between 5 and 6) whereas the SAX type CSPs have a wider application range with respect to the pH and possess also in the neutral pH-range exchanging capacity.

EXAMPLE 7

Standard protocol for the preparation of 9,11-subst.-DHC derivatives used as chiral extractors (chiral carriers) in stereoselective liquid-liquid extraction and related techniques exemplified by the synthesis of O-(1-adamantylcarbamoyl)-11-octadecylsulfinyl-10,11-dihydro-quinidine a.) Synthesis of the precursor O-(1-adamantylcarbamoyl)-quinidine This compound was prepared in analogy to the synthesis protocol as presented for the precursor O-(t.-butylcarbamoyl)-quinine derivative in example 1, a.). Thus, 1-adamantyl isocyanate and quinidine were refluxed in toluene in presence of catalytic amounts of dibutyl tin dilaurate. The crude product was crystallized in ethylacetate.

m.p.: 194–196° C.; $[\alpha]_{Hg546}$=−55.6; (c=1.2; dichloromethane);

IR (KBr): 2911, 1720, 1624, 1506 cm$^{-1}$.

b.) O-(1-adamantylcarbamoyl)-11-octadecylthio-10,11-dihydro-quinidine

This synthesis step follows the general procedure of radical addition of a thiol compound to the vinyl group at the carbon $C_3$ of the quinuclidine of cinchona alkaloids as described by [N. Kobayashi et al., J. Polym. Sci. Polym. Lett. Ed., 20 (1982) 85]. Thus, a solution of O-(1-adamantylcarbamoyl)-quinidine (10 mmol), of octadecan-1-thiol (40 mmol), and AIBN (1.0 mmol) in chloroform (20 ml) was stirred at 70° C. under nitrogen for 24 h. The excess of thiol was removed by flash chromatography with silica gel and chloroform as eluent. Subsequently, the product was eluted with a mixture of chloroform/methanol (8/2). Finally, the crude product was washed with methanol to obtain a white solid in 90% yield.

m.p.: 101–114° C.; $[\alpha]_{Hg546}$=+22.7; (c=1.1; dichloromethane);

IR (KBr): 2920, 2852, 1718, 1622, 1592, 1506, 1362 cm$^{-1}$.

c.) Standard procedure for the oxidation of thioethers to the respective sulfoxides exemplified by the preparation of O-(1-adamantylcarbamoyl)-11-octadecylsulfinyl-10,11-dihydro-quinidine:

When 1.4 g of O-(1-adamantylcarbamoyl)-10,11-dihydro-11-octadecylthio-quinidine was treated with 1.2 equivalents of NalO$_4$ in 180 ml of methanol/water (9:1) at room temperature, the thioether was almost quantitatively oxidized after 3 h. The reaction mixture was diluted with water and the pH of the aqueous solution adjusted to 8.5 with a mixture of NaHCO$_3$/Na$_2$CO$_3$. The product was extracted with chloroform and the residue obtained after evaporation of the solvent purified by flash chromatography (1. ethylacetate; 2. ethylacetate/mehanol). Thus, a pure white solid in 80% yield was obtained.

m.p.: 104–106 °C.; $[\alpha]_{Hg546}$=+31.4; (c=2.0; dichloromethane);

IR (KBr): 3433, 2922, 2854, 1718, 1621, 1594, 1508, 1464, 1434, 1404, 1363, 1340, 1299, 1141, 1087, 1032 cm$^{-1}$.

EXAMPLE 8

Synthesis of a homopolymer containing the 9-subst.-cinchonan skeleton by polymerization of 2-isocyanatoethyl methacrylate (IEMA) and reaction of the polymer with quinine a.) Polymerization of IEMA 1.44 ml (10 mmol) of IEMA were dissolved in 15 ml dry and peroxide free dioxane. 0.5% (w/w) (7.75 mg) of AIBN were added and the mixture polymerized for 7h at 90° C. continuously flushing with nitrogen. After 7h 4.26 g of anhydreous quinine base dissolved in dry dioxane were added. Then the reaction mixture was stirred for 48 h at 70° C. The reaction mixture was allowed to cool to room temperature and after addition of dry diethylether the cinchonan containing polymer precipitated. The polymer was washed several times with ether and methanol. The dried polymer was subjected to IR-analysis which confirmed a complete reaction by absence of the isocyanate band.

IR (KBr): 3420, 2940, 1725, 1620, 1590, 1510 cm$^{-1}$.

Figure 8:
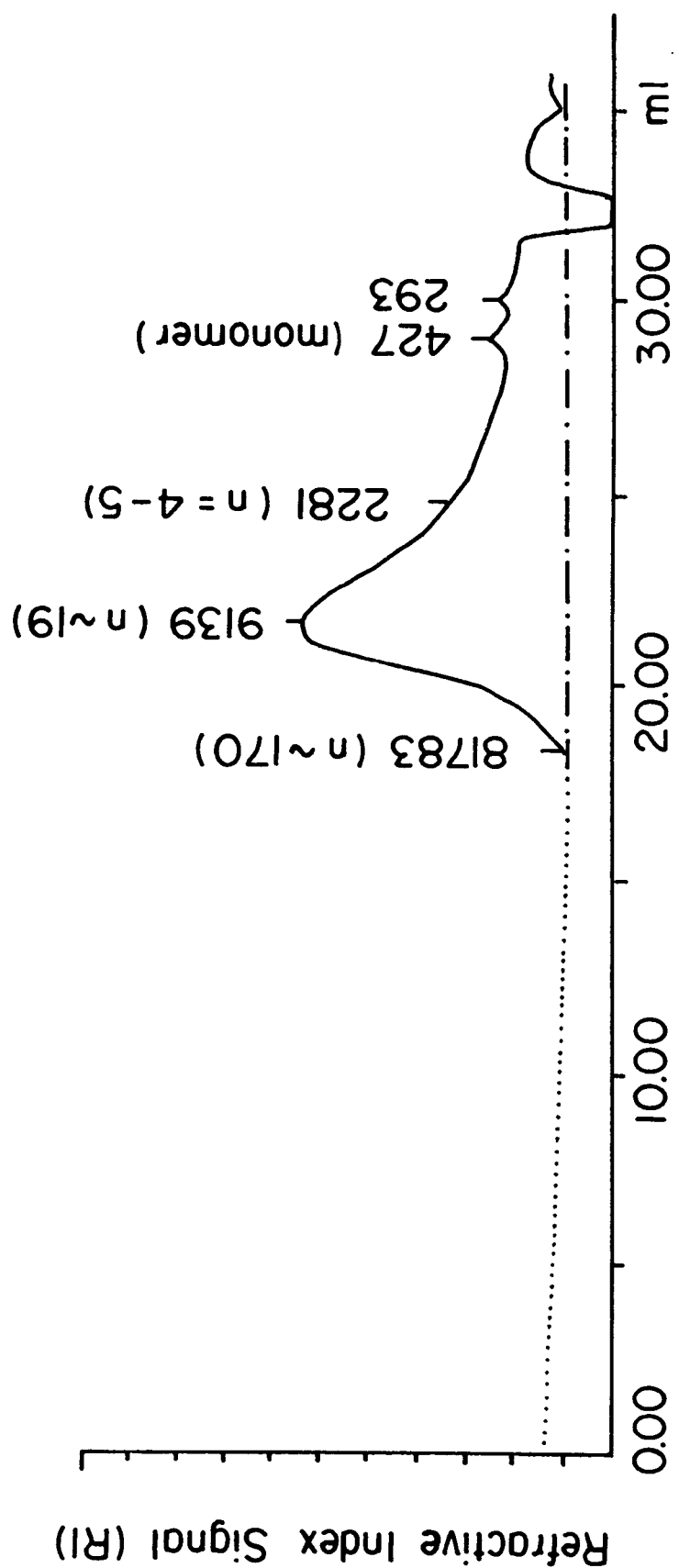
FIG. 8 presents, the molecular weight distribution of the homopolymeric poly-{O-[2-(methacryloyloxy) ethylcarbamoyl]-quinine} determined by GPC using Ultra-Styragel as stationary phase (Chrom. cond.: Mob. phase: THF; flow-rate: 1 ml/min.; as calibration for the molecular mass polystyrene standards were used).

The characterization of this polymer by molecular weight distribution is shown in FIG. 8.

Immobilization of the Homopolymeric Precursor onto Silica by a Coating Procedure (CSP XVII)

4 g of silica (Si100, 7 μm) were suspended in a solution of the 9-subst.-DHC containing homopolymer in dioxane and the suspension sonicated for 5 minutes. Afterwards the solvent was slowly evaporated and the crude modified chiral sorbent washed several times %With diethylether and methanol. CHN-elemental analysis yielded 8.32%C, 1.14%H and 1.0%N; this corresponds to SO-coverage of about 0.25 mmol/g silica. The chiral sorbent was sieved and slurry packed into a stainless-steel HPLC column. At aqueous mobile phase conditions this adsorbed polymeric selector is insoluble and remain stable.

EXAMPLE 9

Synthesis of a Chiral Polymer with Anchor Groups for Immobilization onto Silica by Radical Initiated Copolymerization (CSP XVIII)

a.) Synthesis of O-[2-(methacryloyloxy)ethylcarbamoyl]-11-octadecylsulfinyl-10,11-dihydro-quinidine (monomer A)

11-Octadecylsulfinyl-10,11-dihydroquinidine was synthesized according to the preparation protocols presented in example 7, b.) and c.), but starting with unmodified quinidine. The product, obtained by radical addition of the thiol to quinidine and subsequent oxidation to the corresponding sulfoxide, was dissolved in chloroform. 4-Hydroxyanisol as polymerization inhibitor, dibutyl tin dilaurate as catalyst and 2-isocyanatoethyl methacrylate (IEMA) were added. The reaction mixture was stirred at 50° C. for 10 h. Afterwards, the solvent was evaporated and the residue washed thoroughly with petrolether. The remaining yellow oil was subjected to IR-analysis that confirmed the assumed structure by the presence of the carbonyl band of the carbamate product and the absence of the isocyanate band.

IR (KBr): 2923, 2853, 1721, 1623, 1592 cm$^{-1}$.

b.) Synthesis of pre-polymers by copolymerization of O-[2-(methacryloyloxy)-ethylcarbamoyl]-10,11-dihydro-11-octadecylsulfinyl-quinidine with 3-trimethoxysilyl-propyl methacrylate (monomer B, co-monomer):

2.0 g of monomer A, 50 mg of AIBN and 60 μl of monomer B were dissolved in 40 ml of toluene. The solution was flushed with a soft stream of nitrogen to avoid the presence of oxygen during polymerization. The reaction flask was plunged into a water bath and the temperature kept constant at 80° C. for 2 h. A sample of 500 μl of the reaction mixture was removed and subjected to MALDI-TOF-MS analysis which yielded a polymer distribution up to a polymer grade of n=35 (with similar sub-structure within each polymer grade). Exper. cond.: Concentration: 1.7 mg of polymer in 1 ml THF, matrix 1,8,9-THA (dithranol), polarity: positive, mass range: 700 to 20000 DA, det.: −4.80 kV.

c.) Immobilization of the polymer onto silica:

To the former reaction mixture a suspension of 3 g of porous silica (Kromasil 200–5 μm) in 60 ml toluene was added and the mixture refluxed for 4 h. Then, the suspension was cooled to room temperature and the silica sedimented. The toluene solution was removed and the crude silica washed several times with toluene, THF, chloroform, methanol, petrolether. The dried silica sorbent was subjected to elemental analysis which yielded 13.7%C and 0.83%N.

d.) End-capping of the modified silica:

A suspension of 3 g of the modified chiral sorbent in toluene and 1 ml of N,O-bis-trimethylsilyl acetamide (BSA) were refluxed for 12 h. The clean-up was performed as described above.

e.) A spectrum of applications of this polymeric type chiral anion exchanger for the resolution of the enantiomers of chiral aryloxy, arylthio, and arylamino carboxylic acids is summarized in Tab. 1.

TABLE 1

Chromatographic results of the separation of α-aryloxy, α-arylthio and α-arylamino carboxylic acids obtained on CSP XVIII$^a$.

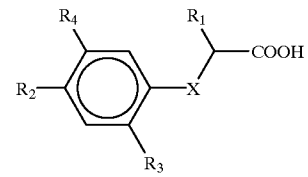

| | CSP XVIII | | | | | | | | |
|---|---|---|---|---|---|---|---|---|---|
| Analyte (SA) | k'$_1$$^b$ | α$^b$ | e.o.$^c$ | Compound | X | R$_1$ | R$_2$ | R$_3$ | R$_4$ |
| 1 | 3.448 | 1.132 | | 1 | —O— | methyl (Me) | H | H | H |
| 2 | 3.469 | 1.127 | | 2 | —O— | ethyl (Et) | H | H | H |
| 3 | 3.662 | 1.222 | | 3 | —O— | Me | Me | H | H |
| 4 | 3.669 | 1.214 | | 4 | —O— | Et | Me | H | H |
| 5 | 3.517 | 1.229 | | 5 | —O— | Me | MeO | H | H |
| 6 | 3.228 | 1.186 | | 6 | —O— | Me | F | H | H |
| 7 | 4.138 | 1.258 | R | 7 | —O— | Me | Cl | H | H |
| 8 | 4.152 | 1.228 | R | 8 | —O— | Et | Cl | H | H |
| 9 | 4.303 | 1.234 | | 9 | —O— | n-propyl | Cl | H | H |
| 10 | 4.083 | 1.176 | | 10 | —O— | iso-propyl | Cl | H | H |
| 11 | 5.159 | 1.229 | | 11 | —O— | n-hexyl | Cl | H | H |
| 12 | 7.586 | 1.147 | S | 12 | —O— | phenyl | Cl | H | H |
| 13 | 4.717 | 1.279 | | 13 | —O— | Me | Br | H | H |
| 14 | 4.586 | 1.251 | | 14 | —O— | Et | Br | H | H |
| 15 | 3.124 | 1.245 | R | 15 | —O— | Me | NMe$_2$ | H | H |
| 16 | 5.366 | 1.514 | R | 16 | —O— | Me | NO$_2$ | H | H |
| 17 | 8.683 | 2.110 | | 17 | —O— | Me | NO$_2$ | NO$_2$ | H |
| 18 | 8.897 | 1.896 | | 18 | —S— | Me | NO$_2$ | NO$_2$ | H |
| 19 | 4.269 | 1.060 | | 19 | —NH— | Me | H | H | H |

TABLE 1-continued

Chromatographic results of the separation of α-aryloxy, α-arylthio and α-arylamino carboxylic acids obtained on CSP XVIII[a].

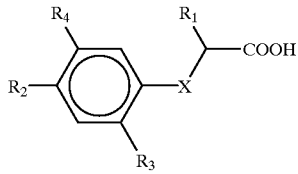

| | CSP XVIII | | | | | | | | |
|---|---|---|---|---|---|---|---|---|---|
| Analyte (SA) | k'$_1$[b] | α[b] | e.o.[c] | Compound | X | R$_1$ | R$_2$ | R$_3$ | R$_4$ |
| Mecoprop | 4.503 | 1.345 | | | | | | | |
| Dichlorprop | 5.490 | 1.500 | R | | | | | | |
| Fenoprop | 6.234 | 1.412 | | | | | | | |
| Trolox methyl ether | 3.572 | 1.104 | S | | | | | | |

[a]Chrom. cond.: Mob. Phase: 80% methanol/20% 0.1M ammonium acetate (pHa = 6.0); T: 25° C.; Flow rate: 1 ml/min.
[b]k'$_1$ = (tr$_1$ − t$_0$)/t$_0$; α = k'$_2$/k'$_1$
[c]e.o.: elution order; configuration of first eluted enantiomer

EXAMPLE 10
Synthesis of a 9,11-subst.-DHC Containing Polymeric Type Chiral CSP by Radical Initiated Copolymerization of the Methacrylate Modified SO with Vinyl Silica (CSP XIX)

a.) Synthesis of O-[methacryloyicarbamoyl]-10,11-dihydro-11-octadecylsulfinyl-quinidine (monomer A):

10,11-Dihydro-11-octadecylsulfinyl-quinidine was synthesized according to the protocols presented in example 7, b.) and c.). 4.6 mmol of the product, obtained by radical addition of the thiol to quinidine and subsequent oxidation to the corresponding sulfoxide, were dissolved in chloroform. 4-Hydroxyanisol (0.01%) as polymerization inhibitor, 5 drops dibutyl tin dilaurate as catalyst and 5.1 mmol methacryloyl isocyanate were added. The reaction mixture was stirred at 50° C. for 24 h. Afterwards, the solvent was evaporated and the residue washed thoroughly with petrolether.

Yield: 86%; IR: 2955, 2935, 2872, 1774, 1741, 1708, 1622, 1593, 1510 cm$^{-1}$.

b.) Synthesis of vinyl modified silica (monomer B, comonomer):

Kromasil200-5 μm was suspended in dried toluene and a solution of trichlorvinylsilane was added to the mixture, which was refluxed 12 h. The modified sorbent was sedimented and the solvent removed. The silica raw material then was thoroughly washed several times with toluene, chloroform, methanol and petrolether. The dried modified silica was subjected to elemental analysis which yielded following results: %C=3.17, %H=0.67.

c.) Copolymerization of the chiral O-[(methacryloyl) carbamoyl]-10,11-dihydroquinidine selector with vinyl modified silica:

2.0 g of O-[methacryloylcarbamoyl]-10,11-dihydro-11-octadecylsulfinyl-quinidine were dissolved in 5 ml of xylene. 5.0 g of vinyl modified silica and 25 ml of dry and peroxide free dioxane were added to this solution. To this homogenous suspension 2% radical initiator (AlBN) (dissolved in dioxane) was added and the mixture sonicated for 3 minutes. The suspension was then evaporated at ambient temperature to yield a viscous paste. The flask was flushed with nitrogen, sealed and the mixture copolymerized at 80° C. for 48 h. The modified chiral sorbent was washed several times with THF, chloroform, methanol and petrolether. The dried silica sorbent was subjected to elemental analysis.

d.) Characterization of the obtained polymeric type chiral anion exchanger by elemental analysis: %C=7.56, %H=1.25, %N=0.35; (this corresponds to a SO-coverage of about 85 μmol 9,11-subst.-dihydroquinidine monomer units/g silica.

EXAMPLE 11
Synthesis of CSP VIII Based on 9,11 subst.-10,11-DHC Skeleton using a Carbamoylated Quinine Selector Derived from (S)-leucine Methyl Ester as Precursor a.) Synthesis of the carbamoylated quinine selector derived from (S)-leucine methyl ester as precursor employing the active ester (p-nitrophenyl carbonate) approach: 2.82 g of (S)-leucine methyl ester hydrochloride was dissolved in 160 ml of pyridine. From this solution 100 ml solvent were distilled off to remove traces of water azeotropically.

7.00 g of quinine O-(4-nitrophenyl) carbonate hydrochloride in 50 ml of chloroform and 2 ml of triethyl amine were added to the above solution at ambient temperature. The mixture became yellow and triethyl amine hydrochloride precipitated from the solution. The progress of the reaction was monitored by TLC (silica) using acetone/toluene (50/50; +1% triethyl amine) as mobile phase. After 2 d stirring at ambiente temperature the suspension was filtered and concentrated under reduced pressure. The crude material (12 g yellow oil) was purified chromatographically on 160 g silica gel using toluene/acetone/triethyl amine (30/20/2) as mobile phase to provide the target compound in early fractions. The fractions containing the product have been concentrated in vacuum. The oily residue was stirred in n-hexane for 18 h to give a white solid. After filtration and drying at 40° C. 4.7 g of the product have been obtained.

Yield: 73% m.p.: 90–92° C.

IR: 1034; 1208; 1230; 1262; 1438; 1471; 1511; 1593; 1624; 1725; 2955 cm$^{-1}$

[α]$_{Na589}$=−1.1; [α]$_{Hg546}$=−2.3; (c=1.0; CHCl$_3$)

b.) Grafting of the 9-subst.-cinchonan selector onto porous 3-mercaptopropyl silanized silica as described in example 1, b.).

(3-mercaptopropyl silanized silica: 4.32% C; 0.81% H)

CHN-analysis: 13.53% C, 1.93% H, 1.20% N; SO-coverage about 0.29 mmol/g silica d.) End-capping of the modified chiral sorbent as described in example 1, c.).

CHN-analysis: 14.37% C, 2.05% H, 1.16% N; Thus, about 60 μmol remaining thiol groups per gram silica were modified with lipophilic hexyl groups.

Synthesis of CSP IX Based on an Amphoteric Carbamoylated 10,11-dihydroquinine Type Selector Derived from (S)-leucine e.) The (S)-leucine ester derivative (see example 11, a.)) had been hydrolized to the corresponding carboxylic acid derivative. Thus, 2.7 g of the (S)-leucine methyl ester derivative were dissolved in 100 ml of methanol and mixed with an aqueous solution of $NaHCO_3/Na_2CO_3$ (5%; pH=10.4). This mixture was stirred for 10 d. Then, the methanol was evaporated and the aqueous solution neutralized (pH=7). NaCl was added until saturation and the aqueous phase extracted several times with dichloromethane. The collected organic phases were dried with $Na_2SO_4$. After filtration, the solvent was evaporated and the residue stirred 3h with n-hexane to give a white solid.

Yield: 1.4 g.
m.p.: 136–138° C.
IR (KBr): 2954, 1726, 1623, 1595, 1510, 1237 $cm^{-1}$.
$[\alpha]_{Na589}=-40$; $[\alpha]_{Hg546}=-74$; (c=0.5; chloroform);

f.) Grafting of the amphoteric carbamoylated quinine SO to porous 3-mercaptopropyl silanized silica as described in example 1, b.).

(3-mercaptopropyl silanized silica: 4.32% C; 0.81% H)
CHN-analysis: 12.46% C, 1.78% H, 1.12% N; SO-coverage about 0.267 mmol/g silica.

g.) End-capping of the modified chiral sorbent as described in example 1, c.).

CHN-analysis: 12.93% C, 1.86% H, 1.11% N; Thus, about 66 μmol remaining thiol groups per gram silica were modified with lipophilic hexyl groups.

EXAMPLE 12

Precursors Obtained by Coupling of Hydrazide and Hydrazine Derivatives with 4-nitrophenoxycarbonyl Activated Quinine a) O-[$N_\beta$-(phenylhydrazido)]-quinine A mixture of 2.00 g 4-nitrophenyl carbonate hydrochloride, 1.10 g phenylhydrazine and 1 ml of triethylamine in 40 ml dry THF was stirred for 3 d under nitrogen at ambient temperature. The reaction mixture was concentrated under reduced pressure. The residual dark orange oil was taken into 50 mL dichloromethane and washed with aqueous 1N NaOH (3×40 mL). After reconcentration of the organic layer the material was purified chromatographically on 60 g silica using acetone-ethyl acetate (2/3) as eluent to yield 1.10 g (63%) of an off-white foam. Crystallization from ethylacetate gave white needles.

m.p.: 160–162° C.
$[\alpha]_{Hg546}=-20.5$; $[\alpha]_{Hg436}=-55.5$, (c=1.1, MeOH);
IR (KBr): 1731 $cm^{-1}$;
$^1$H-NMR (400 MHz,DMSO-d): 9.32 (s, 1H), 8.74 (d, 1H), 7.58 (d, 1H), 7.65 (s, 1H), 7.50 (s, 2H), 7.42 (d, 1H), 7.06 (m, 2H), 6.65 (m, 1H), 6.55 (d, 2H), 6.24 (d, 1H), 5.94 (m, 1H), 5.03 (m, 1H), 3.87 (s, 3H), 3.35 (m, 2H), 3.08 (m, 1H), 2.87 (t, 1H), 2.24 (s, 1H), 1.91/t, 1H), 1.81 (s, 1H), 1.72 (t, 1H) and 1.51 (m, 3H);

O-[$N_\beta$-(Benzoyl)hydrazido]-quinine

To a suspension of 2.00 g quinine 4-nitrophenyl carbonate hydrochloride in dry dioxane was added a solution of 0.57 g benzoic hydrazide in 10 mL dioxane and 1.6 mL of triethylamine. After stirring for 15 h at ambient temperature the heterogenous mixture is concentrated under reduced pressure. The residue was purified chromatographically on 80 g silica gel using acetone. The early fractions are containing the nitrophenol, followed by excess benzoic hydrazide and the more polar target compound. Concentration of the product fractions in vacuum gave 1.00 g (54%) slightly yellowish oil which was dissolved in a small volume of ethyl acetate and precipitated by addition of n-hexane. After stirring for 48 h the solid was filtered and dried in high vavuum at 40° C. to give 630 mg of off-white powder.

m.p.: 138–140° C.;
$[\alpha]_{Hg546}=-22.22$; (c=0.99; MeOH)
IR: 3272; 2931; 1740, 1679, 1624 $cm^{-1}$

EXAMPLE 13

Characterization of CSPs and Related Precursors Thereof

In Tab. 2 and Tab. 3 information is summarized concerning the chemical structures and the physico-chemical properties of a great variety of 9- and 9,11-substituted cinchona alkaloid derivatives which have been synthesized and are part of the present invention.

TABLE 2

Representative list of precursors and related CSPs based on 9-subst.-cinchonan and 9,11-subst.-10,11-dihydrocinchonan, respectively.

| $R_1$ | X | Cinchona alkaloid precursor (9-subst. cinchonan) | physico-chemical properties of selector precursor | CSP # | SO-coverage mmol/g silica | chromatographic data[a] (DNB-Leu)[d] | | |
|---|---|---|---|---|---|---|---|---|
| | | | | | | $k_1'$[b] | $\alpha$[b] | e.o.[c] |
| 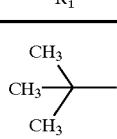 | 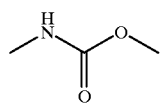 | QN | m.p.: 122° C.; $[\alpha]_{Na589}=-10.9$; $[\alpha]_{Hg546}=-15.8$; (c = 1.01; MeOH); IR (KBr): 1718, 1622, 1593, 1532, 1508, 1267, 1035 $cm^{-1}$; | I | 0.27 | 11.74 | 15.88 | R |
| | | QD | m.p.: 161° C.; $[\alpha]_{Na589}=+0.30$; $[\alpha]_{Hg546}=+0.57$ (c = 1.03; MeOH) IR (KBr): 1725, 1621, 1592, 1506, 1245, 1031 $cm^{-1}$; | | | | | |

TABLE 2-continued

Representative list of precursors and related CSPs based on 9-subst.-cinchonan and 9,11-subst.-10,11-dihydrocinchonan, respectively.

| R₁ | X | Cinchona alkaloid precursor | physico-chemical properties of selector precursor (9-subst. cinchonan) | CSP # | SO-coverage mmol/g silica | chromatographic data[a] (DNB-Leu)[d] | | |
|---|---|---|---|---|---|---|---|---|
| | | | | | | k'₁[b] | α[b] | e.o.[c] |
| 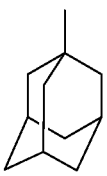 | 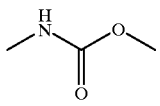 | QN | m.p.: 212–214° C.; [α]$_{Na589}$ = +16.2; [α]$_{Hg546}$ = +17.7 (c = 1.00; CHCl₃) IR (KBr): 2914, 1716, 1621, 1590, 1507, 1471, 1228 cm⁻¹; | | 0.20 | 12.82 | 16.98 | R |
| | | QD | m.p.: 194–196° C.; [α]$_{Hg546}$ = −55.6; (c = 1.2; DCM); IR (KBr): 2911, 1720, 1506, 1624 cm⁻¹; | | | | | |
| 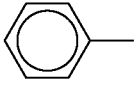 | 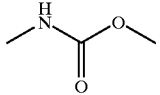 | QN | m.p.: 158–160° C.; [α]$_{Hg546}$ = +84; (c = 1.0; MeOH); IR (KBr): 2949, 1733, 1625, 1551, 1229 cm⁻¹; | | | | | |
| | | QD | m.p.: 220–222° C.; [α]$_{Hg546}$ = +6.0; (c = 1.0; DCM); IR (KBr): 2936, 1736, 1623, 1606, 1228 cm⁻¹; | | | | | |
| 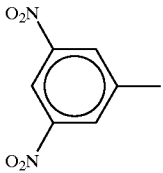 | 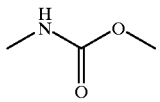 | QN | m.p.: 240–242° C.; [α]$_{Na589}$ = +82; [α]$_{Hg546}$ = +105; (c = 1.03; MeOH); IR(KBr): 2937, 2872, 1741, 1598, 1545, 1513, 1346, 1268, 1245, 1217 cm⁻¹; | II | 0.25 | 13.68 | 4.33 | R |
| | | QD | m.p.: 238° C.; [α]$_{Na589}$ = −80.6; [α]$_{Hg546}$ = −104.5; (c = 1.01; MeOH/AcOH = 40:1); IR (KBr): 2936, 2867, 1737, 1617, 1592, 1550, 1540, 1511, 1247, 1230 cm⁻¹; | III | 0.14 | 6.15 | 3.65 | S |
| 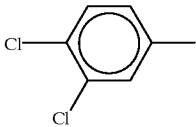 | 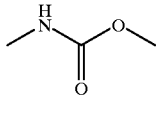 | QD | m.p.: 240° C.; [α]$_{Na589}$ = −73.6; [α]$_{Hg546}$ = −99.5; (c = 1.01; MeOH/AcOH = 19:1); IR (KBr): 2934, 2876, 1720, 1622, 1596, 1540, 1512, 1478, 1241, 1229 cm⁻¹; | | 0.20 | 11.08 | 3.60 | S |
| 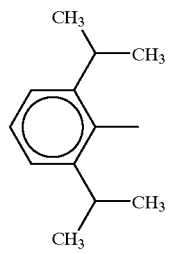 | 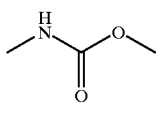 | QN | m.p.: 118° C.; [α]$_{Hg546}$ = +62.0; (c = 1.1; MeOH); IR (KBr): 2961, 2935, 1724, 1624 cm⁻¹; | IV | 0.25 | 6.82 | 3.27 | R |
| | | QD | m.p.: 107–109° C.; [α]$_{Na589}$ = +58.3; [α]$_{Hg546}$ = +68.0; (c = 1.03; CHCl₃); IR (KBr): 2931, 2870, 1721, 1510, 1237, 1037 cm⁻¹; | | | | | |
| 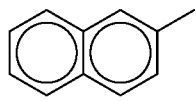 | 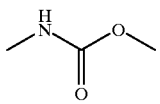 | QN | m.p.: 150–154° C.; [α]$_{Na589}$ = +70.9; [α]$_{Hg546}$ = +81.8; (c = 1.015; DMSO); IR (KBr): 2933, 1723, 1619, 1502, 1298, 1238, 1209 cm⁻¹; | | | 21.00 | 3.52 | R |
| | | QD | m.p.: 168–170° C.; [α]$_{Na589}$ = −11.7; [α]$_{Hg546}$ = −15.6; (c = 1.025; DMSO); IR (KBr): 1727, 1563, 1237, 1222, 1058 cm⁻¹; | | | | | |

TABLE 2-continued

Representative list of precursors and related CSPs based on 9-subst.-cinchonan and 9,11-subst.-10,11-dihydrocinchonan, respectively.

| R₁ | X | Cinchona alkaloid precursor | physico-chemical properties of selector precursor (9-subst. cinchonan) | CSP # | SO-coverage mmol/g silica | k'₁[b] | α[b] | e.o.[c] |
|---|---|---|---|---|---|---|---|---|
| 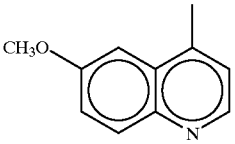 | 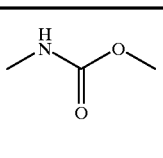 | QN | m.p.: 196–198° C.; $[\alpha]_{Na546}$ = +164.5; $[\alpha]_{Hg436}$ = +371.7; (c = 1.2; MeOH); IR (KBr): 3413, 2939, 1738, 1626, 1510 cm⁻¹; | | | | | |
| 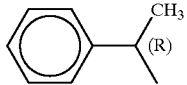 | 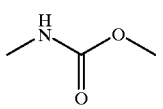 | QN | m.p.: 178–180° C.; $[\alpha]_{Na589}$ = +61.2; $[\alpha]_{Hg546}$ = +72.4; (c = 1.0; CHCl₃); IR (KBr): 2936, 1707, 1622, 1544, 1254, 1051, 1027 cm⁻¹; | V | 0.18 | 7.35 | 3.75 | R |
| | | QD | m.p.: 122–130° C.; $[\alpha]_{Hg546}$ = +198; (c =1.0; MeOH); IR (KBr): 3398, 2928, 2620, 1721, 1621, 1593 cm⁻¹; | VI | 0.20 | 8.02 | 5.33 | S |
| 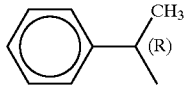 | 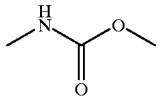 | QN | m.p.: 142–144° C.; $[\alpha]_{Hg546}$ = −41.5; (c = 0.9; DCM); IR (KBr): 3431, 2935, 1712, 1622, 1512 cm⁻¹; | | | | | |
| 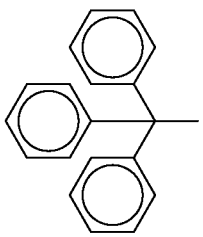 | 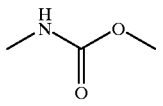 | QN | m.p.: 105–109° C.; $[\alpha]_{Na589}$ = +23.8; $[\alpha]_{Hg546}$ = +27.6; (c = 1.1; CHCl₃); IR (KBr): 1723, 1707, 1486, 1232 cm⁻¹; | VII | 0.20 | 8.21 | 3.70 | R |
| | | QD | m.p.: 94–100° C.; $[\alpha]_{Na589}$ = +49.2; $[\alpha]_{Hg546}$ = +58.5; (c = 0.98; CHCl₃); IR (KBr): 2933, 1733, 1483, 1232, 702 cm⁻¹; | | | | | |
| 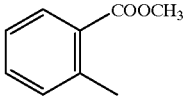 | 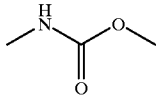 | QN | m.p.: 128–132° C.; $[\alpha]_{Hg546}$ = +74; (c = 1.3; DCM); IR (KBr): 1741, 1693, 1592, 1529, 1266 cm⁻¹; | | 0.26 | 12.90 | 3.01 | R |
| 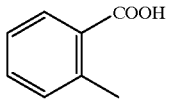 | 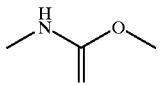 | QN | on-column hydrolized | | 0.26 | | | |
| 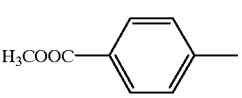 | 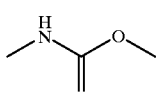 | QN | m.p.: 102–104° C.; $[\alpha]_{Hg546}$ = +79; (c = 1.7; DCM); IR (KBr): 1713, 1602, 1538, 1278 cm⁻¹; | | 0.29 | | | |
| 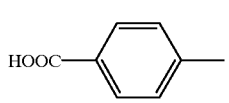 | 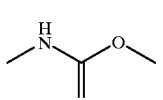 | QN | on-column hydrolized | | 0.29 | | | |
| 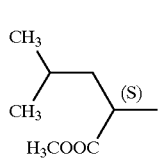 | 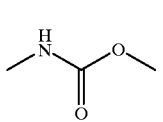 | QN | m.p.: 90–92° C.; $[\alpha]_{Na589}$ = −1.1; $[\alpha]_{Hg546}$ = −2.3; (c = 1.00; CHCl₃); IR (KBr): 2955, 1725, 1624, 1593, 1511, 1471, 1438, 1262, 1230 cm⁻¹; | VIII | 0.29 | | | |

TABLE 2-continued

Representative list of precursors and related CSPs based on 9-subst.-cinchonan and 9,11-subst.-10,11-dihydrocinchonan, respectively.

| $R_1$ | X | Cinchona alkaloid precursor (9-subst. cinchonan) | physico-chemical properties of selector precursor | CSP # | SO-coverage mmol/g silica | chromatographic data[a] (DNB-Leu)[d] $k'_1$[b] | $\alpha$[b] | e.o.[c] |
|---|---|---|---|---|---|---|---|---|
| [CH3-CH(CH3)-CH2-CH(COOH)- (S)] | [methyl N-H carbamate] | QN | m.p.: 136–138° C.; $[\alpha]_{Na589}$ = −40; $[\alpha]_{Hg546}$ = −74; (c = 0.5; CHCl$_3$); IR (KBr): 2954, 1726, 1623, 1595, 1510, 1237 cm$^{-1}$; | IX | | | | |
| [CH3-CH(CH3)-CH2-CH(COOCH2)- (R)] | [methyl N-H carbamate] | QN | m.p.: 118–120° C.; $[\alpha]_{Hg546}$ = +15.0; (c = 2.3; DCM); IR (KBr): 2951, 1750, 1708, 1538, 1264, 1237 cm$^{-1}$; | | | | | |
| [tert-butyl] | [CH2-N(Me)-C(=O)-OMe] | QN | m.p.: 90–91° C.; $[\alpha]_{Na589}$ = −17.4; $[\alpha]_{Hg546}$ = −23.12; (c = 0.86; CHCl$_3$); IR (KBr): 1724, 1264 cm$^{-1}$; | X | 0.23 | 9.50 | 1.59 | R |
| CH$_3$—(CH$_2$)$_3$— | [methyl N-H carbamate] | N$_1$-Methyl-QD | m.p.: 76° C.; $[\alpha]_{Hg548}$ = +43.4; (c = 1.1; DCM) IR (KBr): 3234, 3082, 2928, 2863, 1718, 1622, 1593, 1505 cm$^{-1}$; | XIa | 0.12 | 1.32 | 8.86 | S |
| CH$_3$—(CH$_2$)$_3$— | [methyl N-H carbamate] | QD | m.p.: 60° C.; $[\alpha]_{Na589}$ = +40.7; $[\alpha\pi_{Hg546}$ = +47.0; (c = 1.0113; DCM); IR (KBr): 3340, 2930, 2860, 1720, 1620, 1505 cm$^{-1}$; | XIb | 0.15 | 0.79 | 2.12 | S |
| [tert-butyl] | [N,N'-dimethyl urea] | eQN | m.p.: 136° C.; $[\alpha]_{Hg546}$ = −14; (c = 1.1; MeOH); IR (KBr): 3380, 2961, 2929, 1676, 1625 cm$^{-1}$; | XII | | | | |
| [3,5-dinitrophenyl] | [N-methyl acetamide] | eQN | m.p.: 138–140° C.; $[\alpha]_{Hg546}$ = −72; (c = 2.0; MeOH); IR (KBr): 3423, 2935, 1664, 1625 cm$^{-1}$; | | | | | |
| [4-methylphenyl] | [methyl N-sulfonyl carbamate] | QN | m.p.: 98–100° C.; $[\alpha]_{Na589}$ = +17.08$^a$; $[\alpha]_{Hg546}$ = +16.08; (c = 0.995; CHCl$_3$); IR (KBr): 2942, 1739, 1626, 1280, 1179, 1135 cm$^{-1}$; | | | | | |
| [tert-butyl] | [methyl N-H carbamate] | 9-Methyl-QD | m.p.: 162° C.; $[\alpha]_{Hg546}$ = +23; (c = 1.25; MeOH); IR (KBr): 3254, 2941, 1722, 1680, 1625 cm$^{-1}$; | | | | | |
| [tert-butyl] | [methyl carbamate, reversed] | eQN | m.p.: 82° C.; $[\alpha]_{Hg546}$ = +5.8; (c = 1.0; MeOH); IR (KBr): 3424, 2931, 1708 cm$^{-1}$; | | | | | |

TABLE 2-continued

Representative list of precursors and related CSPs based on 9-subst.-cinchonan and 9,11-subst.-10,11-dihydrocinchonan, respectively.

| R₁ | X | Cinchona alkaloid precursor (9-subst. cinchonan) | physico-chemical properties of selector precursor | CSP # | SO-coverage mmol/g silica | chromatographic data[a] (DNB-Leu)[d] k'₁[b] / α[b] / e.o.[c] |
|---|---|---|---|---|---|---|
| phenyl | methyl hydrazinecarboxylate | QN | m.p.: 160–162° C.; $[\alpha]_{Hg546}$ = −20.5; (c = 1.1; MeOH); IR (KBr): 3328, 2946, 1731, 1624, 1505 cm⁻¹; | | | |
| phenyl | acetyl hydrazine thiocarbamate | QN | m.p.: 138–140° C.; $[\alpha]_{Na589}$ = −15.51; $[\alpha]_{Hg546}$ = −22.22; (c = 0.99; MeOH); IR (KBr): 2931, 1740, 1679, 1511, 1242 cm⁻¹; | | | |
| tert-butyl | methyl carbamate | eQD | m.p.: 128° C.; $[\alpha]_{Hg546}$ = +133; (c = 1.5; MeOH); IR (KBr): 3221, 2939, 2871, 1713, 1623, 1513 cm⁻¹; | | | |
| tert-butyl | methyl carbamate | CD | m.p.: 179–181° C.; $[\alpha]_{Hg546}$ = −4.0; (c = 1.0; MeOH); IR (KBr): 3238, 2931, 1717, 1521, 1458 cm⁻¹; | | | |
| 4-methylphenyl | methanesulfonamide | eQN | m.p.: 82° C.; $[\alpha]_{Hg546}$ = −20; (c = 1.5; MeOH); IR (KBr): 3432, 2927, 1714, 1622, 1328 cm⁻¹; | | | |

[a]Chromatogr. cond.: Mob. phase: 80% MeOH/20% 0.1M ammonium acetate; pha = 6.0; T: 25° C.; flow rate: 1 ml/min.
[b]k'₁ = (tr₁ − t₀)t₀, α k'₂/k'₁
[c]e.o. = elution order: configuration of first eluted enantiomer
[d]DNB-Lew = N-(3,5-dinitrobenzoyl) leucine

TABLE 3

CSPs based on dimeric 9,11-substituted-10,11-dihydrocinchonan selectors.

| R₁ | X₁ = X₂ | Cinchona alkaloid precursor (9-subst. cinchonan) | physico-chemical properties of selector precursor | CSP # | SO-coverage mmol/g silica | k'₁[b] | α[b] | e.o.[c] |
|---|---|---|---|---|---|---|---|---|
| Bridged via R₁: | | | | | | | | |
| —(CH₂)₆— | methyl carbamate | QN | m.p.:134–136° C.; $[\alpha]_{Na589}$ = +1.15; $[\alpha]_{Hg546}$ = +1.83; (c = 1.04; MeOH); IR (KBr): 3363, 2935, 2863, 1720, 1622, 1593, 1510, 1243 cm⁻¹; | XIII | 0.14 | 9.67 | 8.13 | R |
| —(CH₂)₆— | methyl carbamate | QD | m.p.: 153° C.; $[\alpha]_{Na589}$ = +46.1; $[\alpha]_{Hg546}$ = +52.9; (c = 1.02; MeOH); IR (KBr): 1720, 1622, 1593, 1510, 1244, 1030 cm⁻¹; | XIV | 0.12 | 7.68 | 8.65 | S |
| cyclohexylene | methyl carbamate | QN | m.p.: >250° C.; $[\alpha]_{Na589}$ = +36.0; $[\alpha]_{Hg546}$ = +41.0; (c = 1.00; CHCl₃); IR (KBr): 2937, 1719, 1622, 1592, 1509, 1268, 1231, 1034 cm⁻¹; | XV | 0.15 | 14.83 | 7.13 | R |

TABLE 3-continued

CSPs based on dimeric 9,11-substituted-10,11-dihydrocinchonan selectors.

| R₁ | X₁ = X₂ | Cinchona alkaloid precursor | physico-chemical properties of selector precursor (9-subst. cinchonan) | CSP # | SO-coverage mmol/g silica | chromatographic data[a] (DNB-Leu)[d] | | |
|---|---|---|---|---|---|---|---|---|
| | | | | | | $k'_1{}^b$ | $\alpha^b$ | e.o.[c] |
| 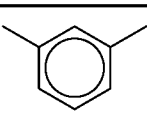 | 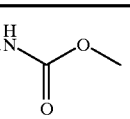 | QN | m.p.: 146–152° C.; $[\alpha]_{Na589}$ = +85; $[\alpha]_{Hg546}$ = +102; (c = 0.99; MeOH); IR (KBr): 3431, 2932, 2865, 1729, 1621, 1545, 1511, 1230 cm$^{-1}$; | XVI | 0.17 | 26.27 | 4.38 | R |

[a]Chromatogr. cond.: Mob. phase: 80% MeOH/20% 0.1M ammonium acetate; pHa = 6.0; T: 25° C.; flow rate: 1 ml/min.
[b]$k'_1 = (tr_1 - t_0)/t_0$, $\alpha = k'_2/k'_1$
[c]e.o. = elution order: configuration of first eluted enantiomer
[d]DNB-Leu = N-(3,5-dinitrobenzoyl) leucine

EXAMPLE 14

Synthesis of CSP XX Based on Non-substituted Quinine and Comparison of Enantioselectivities of this CSP and of a Tert.-butyl Carbamoylated Quinine CSP I as Chiral Anion Exchangers for the Separation of the Enantiomers of a Selected Set of Acidic Chiral Selectands a.) Synthesis of a quinine based CSP with an unsubstituted hydroxyl group at $C_9$:

The synthesis of this CSP was performed in analogy as described for the tert.-butyl carbamoylated CSP in example 1, a.) starting with unmodified quinine base instead of the tert.-butyl carbamoylated derivative thereof. SO-coverage: 0.32 mmol SO/g silica.

b.) Comparison of the chromatographic behaviour of the O-unmodified quinine-CSP with a standard CSP (CSP I) of the present invented CSP type:

The application of an O-unmodified CSP for HPLC enantioseparation has already been described by [Salvadori et al., Chromatographia, 24 (1987) 671]. However, this group did not consider and use this CSP in the reversed phase mode and as chiral anion exchangers, but did evaluate the enantiseparation potential in the normal phase mode only.

As can be seen from Tab. 4 the modification at the $C_9$ hydroxyl group is the directing modulation with respect to distinct binding mode and orientation of the selectand enantiomers toward the selector molecule. This strong effect primarily has be contributed to the carbamate function but also by the bulky tert.-butyl group. The combination of these two stirring groups induce a marked improvement in stereodiscrimination, which is manifested in an extreme and thus unexpected high enantioselectivity observed for DNB-leucine and DNB-valine relative to the data obtained on the unmodified quinine CSP under identical experimental conditions. Supportingly, the inverted order of elution found for these pairs of enantiomers give rise to discuss a different mechanism responsible for chiral recognition for this class of selectands. Enantioseparation capabilities for N-DNP amino acids are compareable for both CSP and also an identical behavior in terms of elution order is observed. However, the trend to exhibit shorter elution times make the use of the CSP presented in this invention more attractive for analytical and preparative application than the unmodified type. Moreover, the trend to exhibit superior enantioseparation potential is not limited to analytes bearing pronounced pi-acidic substituents like N-DNB amino acids, but also includes a broad range of moderately pi-acids and other chiral acids. Separation factors obtained for the agro chemical dichlorprop and the non steriodal anti inflammatory drug suprofen are significantly improved on the carbamate-modified CSP. Excellent enantioseparation obtained for binaphthylphosphate and important N-protected amino acids demonstrate the superior stereodiscriminating properties of the new class of chiral selectors described in this invention.

TABLE 4

Chromatographic results of the separation of the enantiomers of chiral acidic selectands by HPLC using a quinine and a tert.-butyl carbamoylated quinine CSP[a].

| | unmodified Quinine-CSP (CSP XX) | | | tert.-butyl carbamoylated quinine CSP (CSP I) | | |
|---|---|---|---|---|---|---|
| Selectand | $k'_1{}^b$ | $\alpha^b$ | e.o.[c] | $k'_1{}^b$ | $\alpha^b$ | e.o.[c] |
| Dichlorprop | 24.84 | 1.15 | S | 10.94 | 1.19 | S |
| Suprofen | 14.30 | 1.09 | | 10.68 | 1.14 | |
| 1,1'-Binaphthyl-2,2'-diyl hydrogen phosphate | 54.50 | 1.02 | | 35.52 | 1.44 | R |
| DNB-Leu[d] | 28.14 | 1.15 | S | 11.74 | 15.88 | R |
| DNB-Phe[d] | 29.65 | 1.05 | S | 16.19 | 10.78 | R |
| DNB-Ser[d] | 20.33 | 1.06 | R | 10.55 | 5.78 | R |
| DNP-Pro[d] | 33.99 | 1.27 | S | 25.24 | 1.41 | S |
| DNP-Leu[d] | 44.26 | 1.35 | S | 24.01 | 1.31 | S |
| Z-Tyr[d] | 19.17 | 1.05 | R | 12.00 | 1.24 | R |

TABLE 4-continued

Chromatographic results of the separation of the enantiomers of chiral acidic selectands by HPLC using a quinine and a tert.-butyl carbamoylated quinine CSP[a].

| Selectand | unmodified Quinine-CSP (CSP XX) | | | tert.-butyl carbamoylated quinine CSP (CSP I) | | |
|---|---|---|---|---|---|---|
| | $k'_1$[b] | $\alpha$[b] | e.o.[c] | $k'_1$[b] | $\alpha$[b] | e.o.[c] |
| Fmoc-Val[d] | 25.00 | 1.00 | | 15.73 | 1.65 | R |
| Boc-Tyr[d] | 9.87 | 1.00 | | 6.27 | 1.25 | R |

[a]Chromatogr. cond.: Mob. phase: 80% MeOH/20% 0.1M ammonium acetate; pHa = 6.0; T: 25° C.; flow rate: 1 ml/min.
[b]$k'_1 = (t_{r_1} - t_0)/t_0$, $\alpha = k'_2/k'_1$
[c]e.o. = elution order: configuration of first eluted enantiomer
[d]DNB = 3,5-dinitrobenzoyl, DNP = 2,4-dinitrophenyl, Z = benzyloxycarbonyl, Fmoc = 9-fluorenylmethoxycarbonyl, Boc = tert.-butoxycarbonyl

EXAMPLE 15

Influence of N-methylation of the Carbamate Hydrogen on Enantioselectivity

Comparison of N-methyl Tert.-butyl Carbamoylated Quinine Based CSP (CSP X) with the Corresponding Non-methylated CSP (CSP I)

a.) Synthesis of N-methyl tert.-butyl carbamoylated quinine (precursor of CSP X) was performed via the active ester approach according to the standard preparation protocol described in example 11, a.) (physico-chemical properties see Tab. 2).

Figure 9:
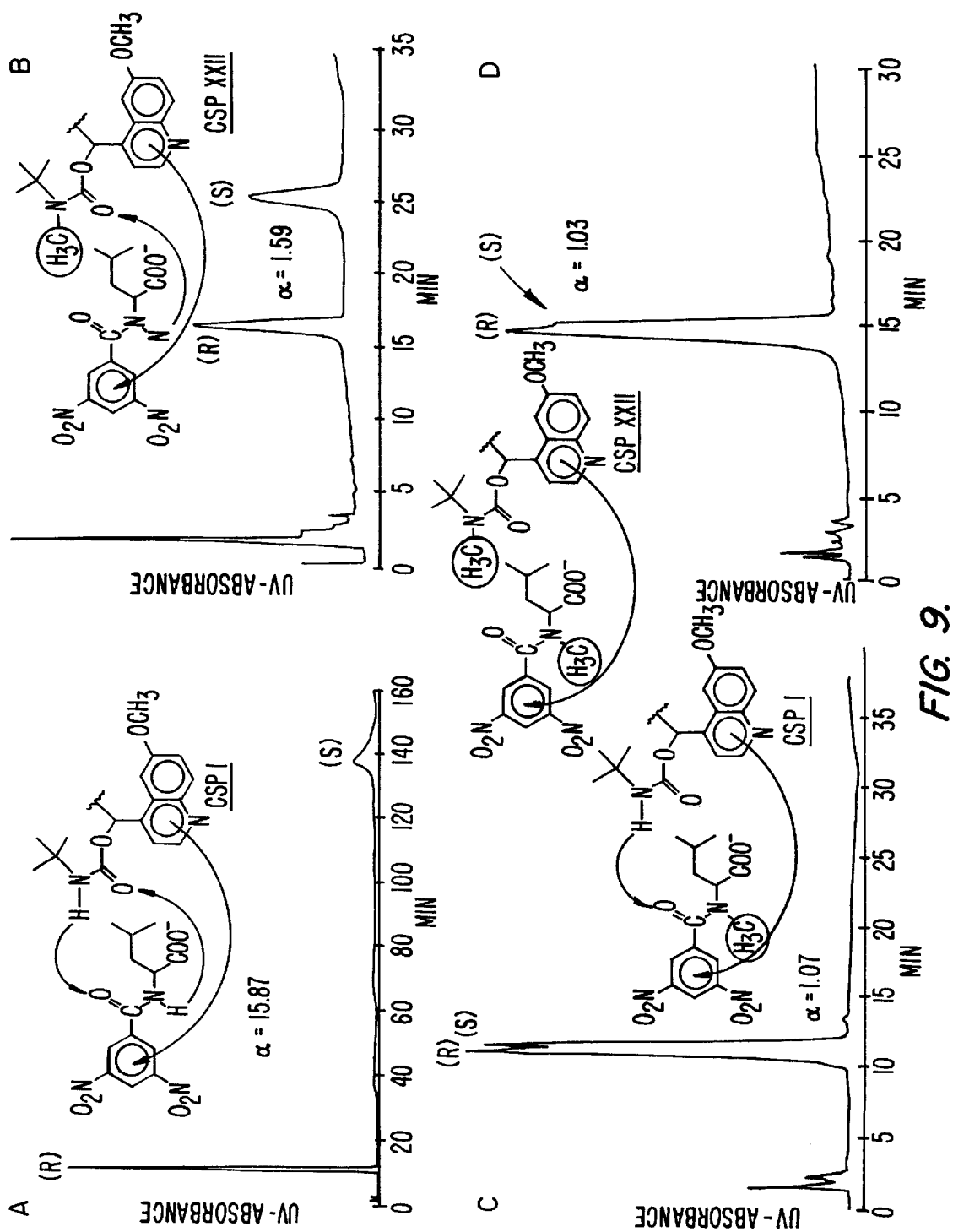
FIG. 9 clearly demonstrates the favorable influence of hydrogen bonding ability of the invented carbamate type CSPs on enantioselectivity for DNB-Leu (see chromatogram A). The effect caused by suppression of the stereocontrolling hydrogen bonding ability by N-methylation of the SO carbamate is illustrated in chromatogram B. (Chromatogr. cond.: see Tab. 2).

Grafting of the precursor onto silica and end-capping was performed according to the protocols of example 1, b.) and c.). The SO-coverage was comparable to that of the non-methylated congener CSP I, namely 0.23 mmol/g silica.

b.) Chromatographic conditions:

A mixture of 80% methanol and 20% 0.1M ammonium acetate was used as standard mobile phase. The pH of the mixture (apparent pH, $pH_a$) was adjusted to 6.0 by adding glacial acetic acid of p.a. quality. The flow rate was 1 ml/min. and temperature was held constantly at 25° C. with a column thermostat. UV detection at 254 nm and 205 nm, respectively, was the standard detection method.

c.) Results:

Interpreting the chromatogram depicted in FIG. 9 it can be conclusively deduced that an undisturbed and unhindered intermolecular hydrogen bonding via the ideal donor acceptor group of an amide moiety at the chiral selector and the selectand compound in co-operation with spatial interactions and ion-pair formation results in an extremely high enantioselectivity (see FIG. 9, A). Using the same selectand but limiting the hydrogen binding by employing the N-methylated carbamoyl selector (see FIG. 9, B) the enantioselectivity drops substantially from $\alpha=15.79$ to $\alpha=1.59$. This set of data demonstrates the impressive potential of amide type CSPs based on the 9,11-subst.-10,11-dihydrocinchonan skeleton and thus the selector types which are part of the present invention.

EXAMPLE 16

Application of 9,11-subst.-DHC-based CSPs as Chiral Anion Exchangers for the Resolution of the Enantiomers of Chiral Acids by HPLC In the following Tables 5 to 10 a number of applications using cinchonan derivative based CSPs, of which the chemical structures are shown in FIG. 10, are summarized demonstrating the potential of the CSPs to be used in ion exchange mode employing aqueous buffered mobile phases.

TABLE 5

Chromatographic results of aryl carboxylic acids[a].

| Compound | CSP I | | CSP II | | CSP III | | CSP IV | | CSP V | | CSP VII | | CSP X | |
|---|---|---|---|---|---|---|---|---|---|---|---|---|---|---|
| | $k'_1$ | $\alpha$ | $k'_1$ | $\alpha$ | $k'_1$ | $\alpha$ | $k'_1$ | $\alpha$ | $k'_1$ | $\alpha$ | $k'_1$ | $\alpha$ | $k'_1$ | $\alpha$ |
| 4-Hydroxy-3-methoxymandelic acid | 2.36 | 1.00 | 2.01 | 1.06 | 1.59 | 1.00 | 2.09 | 1.00 | 2.62 | 1.00 | 1.97 | 1.00 | 2.41 | 1.07 |
| Atrolactic acid | 3.35 | 1.03 | 2.45 | 1.00 | 1.98 | 1.00 | 3.65 | 1.22 | 2.26 | 1.00 | 3.69 | 1.22 | 3.86 | 1.00 |
| 2-Phenyl-2-hydroxybutyric acid | 4.19 | 1.07 | 3.14 | 1.00 | 2.67 | 1.00 | 5.30 | 1.20 | 2.57 | 1.00 | 4.90 | 1.21 | 4.70 | 1.00 |
| 3-Phenyllactic acid | 3.36 | 1.08 | 23.90 | 1.10 | 2.10 | 1.04 | 3.56 | 1.14 | 5.23 | 1.00 | 3.50 | 1.19 | 3.78 | 1.00 |
| 3-(4-Hydroxyphenyl)lactic acid | 2.76 | 1.07 | 2.36 | 1.00 | 1.72 | 1.00 | 2.54 | 1.13 | 2.67 | 1.00 | 2.51 | 1.20 | 1.12 | 1.00 |
| 3-(1-Naphthoxy)lactic acid | 7.08 | 1.06 | 8.14 | 1.28 | 9.74 | 1.13 | 7.92 | 1.14 | 10.61 | 1.01 | 8.90 | 1.14 | 8.16 | 1.08 |
| Tropic acid | 1.83 | 1.02 | 1.40 | 1.04 | 1.18 | 1.00 | 1.74 | 1.08 | 1.45 | 1.00 | 1.72 | 1.05 | 2.03 | 1.02 |

[a]Chrom. cond.: Mobile phase: Acetonitrile/0.1M ammonium acetate (65/35); pHa = 6.0; T = 25° C.; Flow rate = 1 ml/min.; UV 254 nm

TABLE 6

Chromatographic results of aryl carboxylic acids.

| Compound | CSP IV[a] | | | CSP VII[a] | | | CSP X[b] | | |
|---|---|---|---|---|---|---|---|---|---|
| | k'$_1$ | α | e.o.[c] | k'$_1$ | α | e.o.[c] | k'$_1$ | α | e.o.[c] |
| Carprofen | 11.19 | 1.13 | | 9.65 | 1.28 | | 16.52 | 1.04 | |
| Fenoprofen | 6.33 | 1.11 | | 6.42 | 1.06 | | 6.89 | 1.03 | |
| Flurbiprofen | 7.14 | 1.22 | | 7.55 | 1.14 | | 8.76 | 1.08 | |
| Ibuprofen | 4.70 | 1.14 | S | 4.87 | 1.09 | | 4.46 | 1.08 | |
| Ketoprofen | 6.05 | 1.10 | | 5.93 | 1.06 | | 6.12 | 1.05 | |
| Naproxen | 5.58 | 1.20 | S | 5.27 | 1.16 | S | 7.18 | 1.07 | S |
| Pirprofen | 7.11 | 1.21 | | 6.66 | 1.14 | | 8.19 | 1.11 | |
| Suprofen | 7.21 | 1.30 | | 6.82 | 1.19 | | 7.03 | 1.14 | |
| Mosher acid | 6.10 | 1.19 | | 5.80 | 1.39 | | 4.91 | 1.02 | |

[a]Chrom. cond.: Mobile phase: acetonitrile/0.1M ammonium acetate (65/35); pHa = 6.0; T = 25° C. Flow rate = 1 ml/min; Det.: UV 254 nm
[b]Chrom. cond.: Mobile phase: methanol/0.1M ammonium acetate (80/20); pHa = 6.0; T = 25° C.; Flow rate = 1 ml/min; Det.: UV 254 nm
[c]e.o. = elution order: configuration of first eluted enantiomer

TABLE 7

Chromatographic results of N-aryl amino acids[a,b].

| | CSP I | | | CSP III | | | CSP V | | | CSP VI | | |
|---|---|---|---|---|---|---|---|---|---|---|---|---|
| | k'1 | α | e.o.[c] | k'1 | α | e.o.[c] | k'1 | α | e.o.[c] | k'1 | α | e.o.[c] |
| DNP-Ala | 27.11 | 1.19 | | 16.23 | 1.00 | | | | | | | |
| DNP-Ser | 21.11 | 1.42 | | | | | | | | | | |
| DNP-Thr | 16.39 | 1.55 | | | | | | | | | | |
| DNP-Phe | 39.94 | 1.29 | L | 21.35 | 1.00 | | 18.45 | 1.22 | L | 21.44 | 1.20 | D |
| DNP-Val | 20.55 | 1.40 | | | | | | | | | | |
| DNP-Leu | 24.01 | 1.31 | | 12.94 | 1.20 | | 10.67 | 1.27 | | 11.98 | 1.35 | D |
| DNP-N-methyl-Leu | 23.31 | 1.39 | | 10.24 | 1.46 | D | 10.29 | 1.29 | L | 11.52 | 1.40 | D |
| DNP-Pro | | | | | | | | | | | | |
| DNP-AsN | | | | | | | 11.72 | 1.30 | L | | | |
| DNP-Asp | | | | | | | 114.97 | 1.07 | L | | | |
| DNP-GlN | | | | | | | 11.33 | 1.17 | L | | | |
| DNP-Glu | | | | | | | 52.86 | 1.33 | L | | | |
| DNP-Trp | 62.45 | 1.42 | | | | | 33.69 | 1.32 | L | 40.49 | 1.22 | D |
| DNPyr-Ala | | | | 4.01 | 1.00 | | 5.74 | 1.00 | | 5.01 | 1.00 | |
| DNPyr-Phe | 31.62 | 1.18 | | 4.25 | 1.00 | | 5.33 | 1.00 | | 5.04 | 1.00 | |
| DBD-Leu | 15.41 | 1.39 | | 8.86 | 1.00 | | 8.81 | 1.09 | | 9.03 | 1.01 | |
| DBD-Phe | 24.25 | 1.31 | | 13.33 | 1.14 | | 13.54 | 1.15 | | 14.56 | 1.12 | |

| | CSP XIII | | | CSP XV | | | CSP XVI | | |
|---|---|---|---|---|---|---|---|---|---|
| | k'1 | α | e.o.[c] | k'1 | α | e.o.[c] | k'1 | α | e.o.[c] |
| DNP-Ala | 20.67 | 1.25 | L | 32.11 | 1.23 | | 52.24 | 1.11 | |
| DNP-Ser | 18.55 | 1.43 | | 26.35 | 1.43 | L | 41.02 | 1.32 | L |
| DNP-Thr | 14.54 | 1.57 | | 20.53 | 1.55 | | 29.66 | 1.44 | |
| DNP-Phe | 25.31 | 1.43 | L | | | | | | |
| DNP-Val | 16.67 | 1.42 | | 24.70 | 1.40 | | 36.67 | 1.23 | |
| DNP-Leu | 16.24 | 1.39 | L | 26.57 | 1.38 | | 39.02 | 1.23 | |
| DNP-N-methyl-Leu | 15.81 | 1.47 | L | | | | | | |
| DNP-Pro | 18.03 | 1.50 | | 25.33 | 1.46 | | 34.16 | 1.47 | |
| DNP-AsN | 16.17 | 1.40 | | 22.87 | 1.42 | | | | |
| DNP-Asp | | | | | | | | | |
| DNP-GlN | 15.58 | 1.19 | | 21.33 | 1.24 | | 33.33 | 1.13 | |
| DNP-Glu | | | | | | | | | |
| DNP-Trp | | | | | | | | | |
| DNPyr-Ala | | | | 25.69 | 1.01 | | 44.16 | 1.08 | |
| DNPyr-Phe | 24.85 | 1.12 | | 43.57 | 1.09 | | 70.44 | 1.15 | |
| DBD-Leu | 12.36 | 1.23 | | | | | | | |
| DBD-Phe | 19.62 | 1.33 | | | | | | | |

[a]Chrom. cond.: Mobile phase: methanol/0.1M ammonium acetate (80/20); pHa = 6.0; T = 25° C.; Flow rate = 1 ml/min; Det.: UV 254 nm
[b]DNP = 2,4-dinitrophenyl, DNPyr = 3,5-dinitro-2-pyridyl, DBD = 7-dimethylamino-2,1,3-benzoxadiazol-4-yl
[c]e.o. = elution order: configuration of first eluted enantiomer

TABLE 8

Chromatographic results of N-derivatized amino acids[a,b].

| | CSP I | | | CSP II | | | CSP III | | | CSP V | | | CSP VI | | |
|---|---|---|---|---|---|---|---|---|---|---|---|---|---|---|---|
| | $k'_1$ | α | e.o.[c] | k' | α | e.o.[c] | $k'_1$ | α | e.o.[c] | $k'_1$ | α | e.o.[c] | $k'_1$ | α | e.o.[c] |
| DNB-Ala | 10.67 | 8.13 | | 11.50 | 2.09 | | 5.94 | 2.14 | | 7.51 | 2.32 | | 8.28 | 1.28 | |
| DNB-α-Aminobutyric acid | 10.42 | 10.92 | | | | | | | | | | | | | |
| DNB-β-Aminobutyric acid | 12.54 | 8.03 | | | | | | | | | | | | | |
| DNB-β-Aminoisobutyric acid | 30.08 | 3.52 | | | | | | | | | | | | | |
| DNB-Ser | 10.55 | 5.78 | | | | | | | | | | | | | |
| DNB-Thr | 8.99 | 5.81 | | | | | | | | | | | | | |
| DNB-Val | 10.68 | 11.96 | | | | | | | | | | | | | |
| DNB-Ile | 11.94 | 13.22 | | | | | | | | | | | | | |
| DNB-Leu | 11.74 | 15.88 | | 13.68 | 4.33 | | 6.15 | 3.65 | | 7.35 | 3.75 | | 8.02 | 5.33 | |
| DNB-α-methyl-Leu | 16.06 | 1.33 | | 13.27 | 1.30 | | 6.60 | 1.47 | | 7.04 | 1.19 | | 8.19 | 1.17 | |
| DNB-N-methyl-Leu | 10.91 | 1.07 | | 13.50 | 1.00 | | 8.10 | | | 6.19 | 1.01 | | 7.10 | 1.06 | |
| DNB-Pro | | | | | | | | | | | | | | | |
| DNB-Phe | 16.19 | 10.78 | | 20.03 | 2.43 | D | 8.28 | 7.41 | L | 10.31 | 3.64 | D | 11.51 | 5.56 | L |
| DNB-Trp | 29.19 | 8.52 | | 44.72 | 1.48 | D | 14.42 | | | 19.42 | 3.72 | D | 21.61 | 4.76 | L |
| Benzoyl-Ala | | | | 4.32 | 1.12 | D | 2.70 | 1.27 | L | 3.51 | 1.28 | D | 3.31 | 1.30 | L |
| Benzoyl-Leu | 5.60 | 2.56 | | | | | 2.83 | 1.51 | | 3.38 | 1.62 | | | | |
| Benzoyl-Phe | 8.90 | 1.91 | D | 8.76 | 1.30 | D | 4.43 | 1.58 | L | 5.36 | 1.63 | D | 5.11 | 1.47 | L |
| Acetyl-Cys | | | | | | | | | | | | | | | |
| Acetyl-Val | 2.61 | 1.67 | | | | | | | | | | | | | |
| Acetyl-Leu | 2.92 | 1.37 | | | | | | | | | | | | | |
| Acetyl-Phe | 4.45 | 1.38 | D | 3.71 | 1.21 | D | 1.96 | 1.38 | L | 3.04 | 1.18 | D | 2.94 | 1.22 | L |
| Acetyl-Trp | 8.39 | 1.57 | | | | | | | | | | | | | |
| Formyl-Phe | 5.32 | 1.24 | | | | | 2.11 | 1.19 | | 3.67 | 1.09 | | | | |
| DNS-Val | 20.00 | 1.22 | | | | | | | | | | | | | |
| DNS-Thr | 16.51 | 1.30 | | | | | | | | | | | | | |
| DNS-Ser | 17.45 | 1.31 | | | | | | | | | | | | | |
| DNS-Met | 27.32 | 1.15 | | | | | | | | | | | | | |
| DNS-α-Aminobutyric acid | 19.68 | 1.25 | | | | | | | | | | | | | |
| DNS-Leu | 23.09 | 1.00 | | | | | | | | | | | | | |
| DNS-Phe | 35.99 | 1.44 | D | 42.77 | 1.14 | | 15.50 | 1.26 | L | 17.03 | 1.12 | D | 17.08 | 1.25 | L |
| DNS-Trp | 67.55 | 1.00 | | | | | | | | | | | | | |
| DNS-Asp | 185.10 | 1.23 | | | | | | | | | | | | | |

| | CSP XIII | | | CSP XIV | | | CSP XV | | | CSP XVI | | |
|---|---|---|---|---|---|---|---|---|---|---|---|---|
| | $k'_1$ | α | e.o.[c] | $k'_1$ | α | e.o.[c] | $k'_1$ | α | e.o.[c] | $k'_1$ | α | e.o.[c] |
| DNB-Ala | 9.97 | 4.37 | | 8.27 | 4.77 | | 14.14 | 3.52 | | 26.23 | 2.04 | |
| DNB-α-Aminobutyric acid | | | | 7.44 | 6.57 | | 13.48 | 4.94 | | 26.04 | 2.86 | |
| DNB-β-Aminobutyric acid | | | | 8.20 | 6.09 | | 12.40 | 4.62 | | 27.73 | 2.71 | |
| DNB-β-Aminoisobutyric acid | | | | 18.76 | 2.40 | | | | | | | |
| DNB-Ser | 10.08 | 3.85 | D | 8.68 | 4.27 | L | 14.52 | 3.42 | D | 27.62 | 1.94 | D |
| DNB-Thr | 8.44 | 4.47 | | 7.22 | 4.72 | | 12.14 | 4.29 | | 22.04 | 2.56 | |
| DNB-Val | 9.01 | 8.71 | D | 7.38 | 9.28 | | 13.22 | 7.25 | | 24.02 | 3.69 | |
| DNB-Ile | 9.74 | 9.32 | D | 7.59 | 10.09 | | 15.02 | 9.00 | | 27.62 | 4.46 | |
| DNB-Leu | 9.67 | 8.13 | | 7.68 | 8.65 | L | 14.83 | 7.13 | | 26.27 | 4.38 | |
| DNB-α-methyl-Leu | 10.42 | 1.23 | | 8.90 | 1.34 | | | | | | | |
| DNB-N-methyl-Leu | 8.44 | 1.01 | | 7.70 | 1.05 | | | | | | | |
| DNB-Pro | 8.17 | 1.00 | | 5.35 | 1.00 | | 10.77 | 1.00 | | 18.70 | 1.06 | |
| DNB-Phe | 13.59 | 7.90 | D | 11.21 | 8.91 | | 21.39 | 6.94 | | 42.95 | 3.78 | |
| DNB-Trp | 26.92 | 7.47 | D | 21.21 | 8.68 | | | | | | | |
| Benzoyl-Ala | 4.90 | 1.36 | | 4.02 | 1.45 | | | | | | | |
| Benzoyl-Leu | 5.04 | 1.69 | | 3.05 | 1.75 | | | | | | | |
| Benzoyl-Phe | 7.77 | 1.64 | | 6.10 | 1.81 | L | | | | | | |
| Acetyl-Cys | 3.99 | 1.26 | | 2.79 | 1.32 | | | | | | | |
| Acetyl-Val | 2.60 | 1.33 | | 1.73 | 1.43 | | | | | | | |
| Acetyl-Leu | 2.76 | 1.14 | | 1.81 | 1.24 | | | | | | | |
| Acetyl-Phe | 4.33 | 1.27 | | 2.72 | 1.53 | | | | | | | |
| Acetyl-Trp | 8.67 | 1.32 | | 6.62 | 1.44 | | | | | | | |
| Formyl-Phe | 5.01 | 1.15 | | 3.49 | 1.22 | | | | | | | |
| DNS-Val | | | | | | | 21.56 | 1.11 | D | 24.95 | 1.11 | D |
| DNS-Thr | | | | | | | 18.77 | 1.17 | | 21.68 | 1.24 | |
| DNS-Ser | | | | 9.85 | 1.31 | | 20.33 | 1.20 | | 24.28 | 1.36 | |
| DNS-Met | | | | | | | | | | | | |
| DNS-α-Aminobutyric acid | | | | | | | | | | | | |
| DNS-Leu | | | | | | | 22.04 | 1.05 | | 26.92 | 1.05 | |
| DNS-Phe | 29.04 | 1.31 | | | | | 40.70 | 1.31 | | 51.40 | 1.56 | |
| DNS-Trp | 28.85 | 1.31 | | | | | | | | | | |
| DNS-Asp | | | | | | | | | | | | |

[a]Chrom. cond.: Mobile phase: methanol/0.1M ammonium acetate (80/20); pHa = 6.0; T = 25° C.; Flow rate = 1 ml/min; Det.: UV 254 nm
[b]DNB = 3,5-dinitrobenzoyl, DNS = dansyl
[c]e.o. = elution order: configuration of first eluted enantiomer

TABLE 9

Chromatographic results of N-derivatized amino acids[a,b].

| | CSP I | | | CSP III | | | CSP V | | | CSP VI | | | CSP XIII | | |
|---|---|---|---|---|---|---|---|---|---|---|---|---|---|---|---|
| | $k'_1$ | α | e.o.[c] | $k'_1$ | α | e.o.[c] | $k'_1$ | α | e.o.[c] | $k'_1$ | α | e.o.[c] | $k'_1$ | α | e.o.[c] |
| Fmoc-Ala | | | | 6.60 | 1.00 | | 8.94 | | | 8.09 | 1.00 | | 12.95 | 1.25 | |
| Fmoc-Val | | | | | | | | | | | | | 12.27 | 1.67 | |
| Fmoc-Leu | | | | | | | | | | | | | 12.78 | 1.42 | |
| Fmoc-Met | | | | | | | | | | | | | 17.45 | 1.40 | |
| Fmoc-GlN | | | | | | | | | | | | | 10.88 | 1.34 | |
| Fmoc-AsN | | | | | | | | | | | | | 12.92 | 1.25 | |
| Fmoc-Cys | 15.51 | 1.62 | D | | | | | | | | | | | | |
| Fmoc-Cys-S-trityl | 55.89 | 1.43 | D | | | | | | | | | | | | |
| Fmoc-Arg | 1.14 | 1.68 | D | | | | | | | | | | | | |
| Fmoc-Arg-PMC | 21.40 | 1.60 | D | | | | | | | | | | | | |
| Fmoc-Phe | | | | 11.93 | 1.47 | L | 12.95 | 1.28 | D | 13.47 | 1.31 | L | 22.24 | 1.44 | |
| Fmoc-Tyr | | | | | | | | | | | | | 24.32 | 1.49 | |
| Fmoc-Trp | | | | | | | 25.74 | 1.30 | D | 26.94 | 1.29 | L | | | |
| DNZ-Leu | 8.61 | 2.76 | | | | | | | | | | | | | |
| DNZ-Pro | 7.52 | 1.21 | | | | | | | | | | | | | |
| DNZ-2-methyl-taurin | 5.00 | 1.92 | | | | | | | | | | | | | |
| DNZ-α-aminobutyric acid | 6.95 | 2.46 | | | | | | | | | | | | | |
| DNZ-β-aminobutyric acid | 5.21 | 2.18 | | | | | | | | | | | | | |
| DNZ-β-aminoisobutyric acid | 6.32 | 1.97 | | | | | | | | | | | | | |
| DNZ-baclofen | 9.17 | 1.00 | | | | | | | | | | | | | |
| DNZ-α-methyl-Leu | 8.34 | 1.11 | | | | | | | | | | | | | |
| DNZ-N-methyl-Leu | 7.70 | 1.13 | | | | | | | | | | | | | |
| DNZ-N-methyl-Val | 6.60 | 1.17 | | | | | | | | | | | | | |
| DNZ-Asp | 84.32 | 1.03 | | | | | | | | | | | | | |
| DNZ-Glu | 43.34 | 1.82 | | | | | | | | | | | | | |
| DNZ-Lys | 16.89 | 2.18 | | | | | | | | | | | | | |
| DNZ-citrulline | 5.24 | 2.26 | | | | | | | | | | | | | |
| DNZ-Arg | 0.90 | 2.13 | | | | | | | | | | | | | |
| NZ-His | 2.14 | 1.40 | | | | | | | | | | | | | |
| Z-Ala | 6.43 | 1.15 | | 2.51 | 1.03 | L | 3.96 | 1.03 | | 3.73 | 1.10 | L | 5.62 | 1.09 | |
| Z-Leu | | | | 2.84 | 1.06 | | 3.83 | 1.08 | | | | | 5.88 | 1.15 | |
| Z-Val | | | | | | | | | | | | | 5.55 | 1.30 | |
| Z-Ser | 6.10 | 1.21 | | | | | | | | | | | 5.81 | 1.15 | |
| Z-Pro | 6.00 | 1.00 | | | | | | | | | | | 5.35 | 1.00 | |
| Z-Phe | | | | 4.82 | 1.18 | L | 6.54 | 1.13 | D | 6.32 | 1.21 | L | 10.17 | 1.22 | |
| Z-Tyr | 12.00 | 1.24 | | | | | | | | | | | 11.06 | 1.23 | |
| Boc-Ala | 3.33 | 1.12 | | | | | | | | | | | 2.96 | 1.07 | |
| Boc-Leu | 3.72 | 1.21 | D | | | | | | | | | | 3.02 | 1.11 | |
| Boc-Val | 3.55 | 1.40 | | | | | | | | | | | 2.93 | 1.23 | |
| Boc-Ser | | | | | | | | | | | | | 6.72 | 1.00 | |
| Boc-Asp(OBz) | | | | | | | | | | | | | 6.79 | 1.12 | |
| Boc-Arg(Tos) | 5.84 | 1.18 | | | | | | | | | | | 5.79 | 1.12 | |
| Boc-Phe | 6.68 | 1.22 | | | | | | | | | | | 5.38 | 1.19 | |
| Boc-Tyr | 6.27 | 1.25 | | 2.09 | 1.00 | | 4.24 | 1.00 | | | | | 5.77 | 1.19 | |

| | CSP XIV | | | CSP XV | | | CSP XVI | | |
|---|---|---|---|---|---|---|---|---|---|
| | $k'_1$ | α | e.o.[c] | $k'_1$ | α | e.o.[c] | $k'_1$ | α | e.o.[c] |
| Fmoc-Ala | 7.23 | 1.29 | | 15.67 | 1.23 | | 19.72 | 1.13 | |
| Fmoc-Val | | | | | | | | | |
| Fmoc-Leu | 7.56 | 1.43 | | 16.28 | 1.40 | D | 21.50 | 1.24 | D |
| Fmoc-Met | | | | | | | | | |
| Fmoc-GlN | 6.42 | 1.34 | | | | | | | |
| Fmoc-AsN | | | | | | | | | |
| Fmoc-Cys | | | | | | | | | |
| Fmoc-Cys-S-trityl | | | | | | | | | |
| Fmoc-Arg | | | | | | | | | |
| Fmoc-Arg-PMC | | | | | | | | | |
| Fmoc-Phe | 12.99 | 1.49 | | 30.72 | 1.41 | | 41.67 | 1.37 | |
| Fmoc-Tyr | | | | | | | | | |
| Fmoc-Trp | | | | | | | | | |
| DNZ-Leu | | | | | | | | | |
| DNZ-Pro | | | | | | | | | |
| DNZ-2-methyl-taurin | | | | | | | | | |
| DNZ-α-aminobutyric acid | | | | | | | | | |
| DNZ-β-aminobutyric acid | | | | | | | | | |
| DNZ-β-aminoisobutyric acid | | | | | | | | | |
| DNZ-baclofen | | | | | | | | | |
| DNZ-α-methyl-Leu | | | | | | | | | |
| DNZ-N-methyl-Leu | | | | | | | | | |
| DNZ-N-methyl-Val | | | | | | | | | |
| DNZ-Asp | | | | | | | | | |

TABLE 9-continued

Chromatographic results of N-derivatized amino acids[a,b].

| | | |
|---|---|---|
| DNZ-Glu | | |
| DNZ-Lys | | |
| DNZ-citrulline | | |
| DNZ-Arg | | |
| NZ-His | | |
| Z-Ala | | |
| Z-Leu | 3.38 | 1.19 |
| Z-Val | | |
| Z-Ser | 3.64 | 1.19 |
| Z-Pro | | |
| Z-Phe | | |
| Z-Tyr | | |
| Boc-Ala | 1.91 | 1.11 |
| Boc-Leu | 1.78 | 1.16 |
| Boc-Val | 1.89 | 1.25 |
| Boc-Ser | | |
| Boc-Asp(OBz) | 4.40 | 1.17 |
| Boc-Arg(Tos) | 3.54 | 1.14 |
| Boc-Phe | | |
| Boc-Tyr | 3.48 | 1.23 |

[a]Chrom. cond.: Mobile phase: methanol/0.1M ammonium acetate (80/20); pHa = 6.0; T = 25° C.; Flow rate = 1 ml/min; Det.: UV 254 nm
[b]Fmoc = 9-fluorenylmethoxycarbonyl, DNZ, NZ, Z = 3,5-dinitro-, 4-nitro-, benzyloxycarbonyl, Boc = t.-butoxycarbonyl, PMC = pentamethylchroman
[c]e.o. = elution order: configuration of first eluted enantiomer

TABLE 10

Chromatographic data of diverse acidic and neutral chiral compounds[a].

| | CSP I | | | CSP III | | | CSP IV | | | CSP V | | |
|---|---|---|---|---|---|---|---|---|---|---|---|---|
| | $k'_1$ | α | e.o.[b] | $k'_1$ | α | e.o.[b] | $k'_1$ | α | e.o.[b] | $k'_1$ | α | e.o.[b] |
| Dihydro orotic acid | 3.52 | 1.05 | S | | | | | | | | | |
| Tetrahydro-2-furoic acid | 4.50 | 1.08 | | | | | | | | | | |
| 2,3-Dihydropyran-2-carboxylic acid | | | | | | | | | | | | |
| Etodolac | 8.15 | 1.20 | | | | | | | | | | |
| 4-(6-Methyl-2-naphthyl)-4-oxo-2-(methylthio)butyric acid | 20.80 | 1.66 | | | | | | | | | | |
| 1,3,6-Trimethyl-4-(2-napthyl)-1,2,3,4-tetrahydropyrimidine-5-carboxylic acid | 7.31 | 1.59 | R | 5.51 | 1.11 | S | 8.36 | 1.28 | R | 3.63 | 1.22 | |
| 2,6-Dimethyl-4-(3-nitrophenyl)-1,4-dihydropyridine-3,5-dicarboxylic acid monomethylester | 2.41 | 1.00 | | 1.26 | 1.06 | | | | | 1.44 | 1.00 | |
| Citronellic acid | | | | | | | | | | | | |
| 2-t-Butyl-2-methyl-1,3-benzodioxolan-4-carboxylic acid | 5.02 | 1.06 | | | | | | | | | | |
| Proglumide | | | | 1.67 | 1.16 | | | | | 1.66 | 1.17 | |
| Abscisic acid | 2.88 | 1.00 | | 1.15 | 1.00 | | | | | 1.63 | 1.00 | |
| Ca-Folinate | | | | 48.23 | 1.00 | | | | | 54.49 | 1.14 | |
| Ciprofibrate | 15.62 | 1.04 | R | 5.00 | 1.00 | | | | | 5.83 | 1.00 | |
| Sulindac | | | | 12.40 | 1.00 | | | | | 6.73 | 1.00 | |
| 6,6'-Dimethyl-2,2'-biphenyl dicarboxylic acid | | | | 2.68 | 1.05 | S | | | | | | |
| Warfarin | | | | 3.22 | 1.00 | | | | | | | |
| Acenocoumarol | | | | 5.84 | 1.00 | | | | | | | |
| Campher-10-sulforic acid | | | | | | | | | | 0.81 | 1.00 | |
| α-(p-Hydroxyphenyl)sulfoacetic acid | | | | | | | | | | | | |
| 1,1'-Binaphthyl-2,2'-diyl hydrogenphosphate | 35.52 | 1.44 | R | 17.48 | 1.29 | S | | | | 18.03 | 1.26 | |
| Mofebutazone | 4.84 | 1.16 | | | | | | | | | | |
| Sulfinpyrazone | 8.52 | 1.09 | | | | | | | | | | |
| cis-Chrysanthemic acid | 1.18 | 1.27 | | | | | | | | | | |
| trans-Chrysanthemic acid | 1.82 | 1.20 | | | | | | | | | | |
| 2-Hydroxybutyric acid | 3.86 | 1.08 | | | | | | | | | | |
| 3-Hydroxybutyric acid | 1.89 | 1.16 | | | | | | | | | | |
| Omeprazole | | | | 0.71 | 1.17 | | | | | | | |
| Partoprazole | | | | 0.51 | 1.19 | | | | | 0.41 | 1.00 | |
| cis-Cyclohexane-1,2-dicarboxylic acid monomethylester | 1.36 | 1.00 | | | | | | | | | | |
| cis-Cyclohexane-1,2-dicarboxylic acid monobenzylester | 2.45 | 1.07 | | | | | | | | | | |
| trans-Cyclohexane-1,2-dicarboxylic acid monomethylester | 1.41 | 1.07 | | | | | | | | | | |
| trans-Cyclohexane-1,2-dicarboxylic acid | 4.24 | 1.06 | | | | | | | | | | |
| N-(3,5-Dinitrobenzoyl)-1-naphthylethylamide | | | | 2.30 | 1.14 | S | | | | | | |
| N-(1-Naphthoyl)-4-nitrophenylethylamide | | | | 1.11 | 1.08 | S | | | | | | |
| N-(1-Naphthoyl)-1-naphthylethylamide | | | | 1.69 | 1.34 | S | | | | | | |

TABLE 10-continued

Chromatographic data of diverse acidic and neutral chiral compounds[a].

|  | CSP VI | | | CSP XIII | | | CSP XIV | | |
|---|---|---|---|---|---|---|---|---|---|
|  | $k'_1$ | α | e.o.[b] | $k'_1$ | α | e.o.[b] | $k'_1$ | α | e.o.[b] |
| Dihydro orotic acid | | | | 3.48 | 1.00 | | | | |
| Tetrahydro-2-turoic acid | | | | 4.25 | 1.00 | | | | |
| 2,3-Dihydropyran-2-carboxylic acid | | | | 5.69 | 1.08 | | | | |
| Etodciac | | | | 7.55 | 1.12 | | | | |
| 4-(6-Methyl-2-naphthyl)-4-oxo-2-(methylthio)butyric acid | | | | 20.72 | 1.33 | | 10.73 | 1.38 | |
| 1,3,6-Trimethyl-4-(2-napthyl)-1,2,3,4-tetrahydropyrimidine-5-carboxylic acid | 3.458 | 1.299 | S | 6.86 | 1.35 | R | | | |
| 2,6-Dimethyl-4-(3-nitrophenyl)-1,4-dihydropyridine-3,5-dicarboxylic acid monomethylester | 1.306 | 1.000 | | | | | | | |
| Citronellic acid | | | | 6.20 | 1.00 | | | | |
| 2-t-Butyl-2-methyl-1,3-benzodoxolan-4-carboxylic acid | | | | 4.72 | 1.02 | | 2.43 | 1.08 | |
| Proglumide | 1.590 | 1.074 | | | | | | | |
| Abscisic acid | | | | | | | | | |
| Ca-Folurate | | | | | | | | | |
| Ciprofibrate | | | | | | | | | |
| Sufindac | | | | | | | | | |
| 6,6'-Dimethyl-2,2'-biphenyl dicarboxylic acid | | | | | | | | | |
| Warfarin | 3.472 | 1.000 | | 6.33 | 1.00 | | | | |
| Aceroccumarol | 6.951 | 1.090 | | | | | | | |
| Campher-10-sulforic acid | | | | | | | | | |
| α-(p-Hydroxyphenyl)sulfoacetic acid | | | | | | | | | |
| 1,1'-Binaphthyl-2,2'-dyl hydrogenphosphate | | | | | | | | | |
| Molebutazone | | | | | | | 2.42 | 1.50 | |
| Sulfinpyrazone | | | | | | | 4.10 | 1.00 | |
| cis-Chrysanthemic acid | | | | | | | | | |
| trans-Chrysanthemic acid | | | | | | | | | |
| 2-Hydroxybutyric acid | | | | | | | | | |
| 3-Hydroxybutyric acid | | | | | | | | | |
| Omeprazole | | | | | | | | | |
| Partoprazole | | | | | | | | | |
| cis-Cyclohexane-1,2-dicarboxylic acid monomethylester | | | | | | | | | |
| cis-Cyclohexane-1,2-dicarboxylic acid monobenzylester | | | | | | | | | |
| trans-Cyclohexane-1,2-dicarboxylic acid monomethylester | | | | | | | | | |
| trans-Cyclohexane-1,2-dicarboxylic acid | | | | | | | | | |
| N-(3,5-Dinitrobenzoyl)-1-naphthylethylamide | | | | | | | | | |
| N-(1-Naphthoyl)-4-nitrophenylethylamide | | | | | | | | | |
| N-(1-Naphthoyl)-1-naphthylethylamide | | | | | | | | | |

[a]Chrom. cond.: Mobile phase: methanol/0.1M ammonium acetate (80/20); pHa = 6.0; T = 25° C.; Flow rate = 1 ml/min, Det.: UV 254 nm
[b]e.o. = elution order: configuration of first eluted enantiomer

EXAMPLE 17

Fractionated Crystallization of 3,5-dinitrobenzoylated Leucine (DNB-Leu) Racemate Employing O-(t.-butylcarbamoyl)-quinine as Chiral Resolving Agent a.) Synthesis of the chiral selector see example 1, a.).

b.) 25 mg of rac. DNB-Leu (Sigma Chemicals) was dissolved in 0.5 ml of 2-propanol and an equimolar amount of the chiral resolving agent (37 mg dissolved in 0.5 ml 2-propanol) was added. The solution was heated and filtered. Then, the mixture was allowed to crystallize overnight at room temperature. The solid precipitate was collected by filtration and yielded after thoroughly washing and drying 21 mg of white or slightly yellow crystals. This corresponds to an overall chemical yield of 33.7%.

c.) The DNB-Leu enantiomer composition as well as the absolute configuration of the optically enriched enantiomer was determined by subjecting a sample of the crystals to an HPLC system employing the O-(t-butyicarbamoyl)-quinine based CSP (see example 1 and 2). The chiral analysis furnished an enantiomer ratio (determined via the peak area ratio of the both enantiomers) of 2.5% of DNB-D-Leu (first eluting) to 97.5% of DNB-L-Leu (second eluting) and the corresponding ee-value of thus obtained, respectively enriched, DNB-L-Leu enantiomer was determined to be 95%. For a single crystallization step, this is an exceptionally good optical yield. This example demonstrate the great potential of the present invented chiral selectors and auxiliaries for fractionated crystallization via diastereomeric salt formation thus being a very efficient method for the preparative separation and isolation of acidic selectands exemplified with DNB-Leu (this and some other applications are summarized in Tab. 11). Via conventional methods the individual selectors and selectands can be recovered employing acid/base controlled extraction protocols.

TABLE 11

Successful resolutions of racemic carboxylic acids by fractionated crystallization using present invented cinchonan carbamates.

| SA | SO | crystall. step | solvent | % ee | yield (%) |
|---|---|---|---|---|---|
| DNB-Leu | t-BuCQN[a] | 1 | 2-propanol | 95.0 | 40 |
| DNB-Leu | t-BuCQN[a] | 1 | acetone | 99.0 | 40 |
| DNB-Leu | PCQN[b] | 1 | diisopropylether/acetone | 85.0 | 35 |
| NM97/134[c] | DiPPCQN[d] | 1st | diisopropylether/acetone | 74.6 | 75.0 |
|  |  | 2nd | diisopropylether/acetone | 92.8 | 43.3 |
|  |  | 3rd | diisopropylether/acetone | 99.4 | 35.0 |
| α-Ethylhexanoic acid | DiPPCQN[d] | 1st | diisopropylether/acetone | 13.0 | 85.0 |

[a]tBuCQN = O-[(tert.-butyl)carbamoyl]-quinine
[b]PCQN = O-[(phenyl)carbamoyl]-quinine
[c]research compound
[d]DiPPCQN = O-[(2,6-diisopropylphenyl)carbamoyl]-quinine

EXAMPLE 18
Resolution of Amino Acid Derivatives by Liquid-liquid Extraction Technique and Stereoselective Ion-pair Formation Enantioselective extraction was achieved by adding a chiral selector or carrier (SO) with the 9,11-subst.-DHC skeleton, e.g. O-(1-adamantylcarbamoyl)-11-octadecylsulfinyl-10,11-dihydro-quinidine or any other chiral extractor of the present invention (more details are documented in Tab. 12), to the extract phase which enhances preferentially the solubility of only one SA-enantiomer into this phase, whereas the other SA-enantiomer remains preferentially in the raffinate phase. Different distribution rates and association/dissociation constants of the diastereomeric SO-SA molecule associates in the raffinate and the extract phase are responsible for stereoselective separation process leading to efficient optical resolution.

Two phase partition experiments were carried out with the racemic mixture of DNB-Lue and an equimolar ratio of O-(1-adamantyicarbamoyl)-11-octadecylsulfinyl-10,11-dihydro-quinidine. Thus 0.75 ml of a 1 mM solution of the racemic SAs in ammonium acetate buffer were mixed with 0.15 ml of a 2.5 mM solution of the chiral selector in dodecane. After extraction and phase separation the concentration of the individual enantiomers in the aqueous donor phase was determined by enantioselective HPLC-analysis using CSP I. The enantiomeric purity of DNB-D-Leu obtained by conventional back-extraction of the raffinate phase was >95% ee and an overall yield of 70% was achieved in a single extraction step.

Stereoselective liquid-liquid extraction data obtained with other 9,11-subst.-DHC extractors and DNB-Leu presented in this invention are documented in Tab. 12.

TABLE 12

Chiral carriers and extractors based on 9,11-subst.-10,11-dihydrocinchonan derivatives used for stereoselective liquid—liquid extraction.

| R1 | X | Y | R4 | cinchona alkaloid precursor | physico-chemical properties of chiral extractors (9,11-subst.-DHC derivatives) | extraction experiments[a] q[b] | ee % |
|---|---|---|---|---|---|---|---|
| 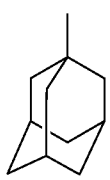 | 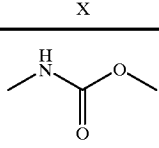 | —S— | —(CH$_2$)$_{17}$—CH$_3$ | QN | m.p.: 82–89° C.; [α]$_{Hg436}$ = −3.0; (c = 1.1; DCM); IR (KBr): 2922, 2852, 1714, 1622, 1591, 1509, 1363 cm$^{-1}$; | 9.00 | 80.0 |
|  |  |  |  | QD | m.p.: 110–114° C.; [α]$_{Hg546}$ = +22.7; (c = 1.1; DCM); IR (KBr): 2920, 2852, 1718, 1622, 1592, 1506, 1362 cm$^{-1}$; | 8.40 | 79.0 |
| 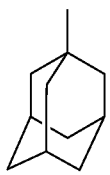 | 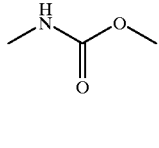 |  | —(CH$_2$)$_{17}$—CH$_3$ | QN | yellow oil; [α]$_{Hg546}$ = −5.0; (c = 1.0; DCM) IR (KBr): 3280, 2922, 2852, 1715, 1622, 1360 cm$^{-1}$; | 9.32 | 81.0 |
|  |  |  |  | QD | m.p.: 104–106° C.; [α]$_{Hg546}$ = +31.4; (c = 2.0; DCM) IR (KBr): 2922, 2854, 1718, 1363, 1340 cm$^{-1}$; | 9.50 | 82.0 |
| 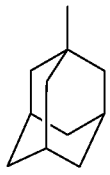 | 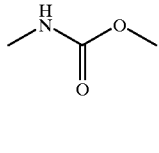 |  | —(CH$_2$)$_{17}$—CH$_3$ | QN | m.p.: 52–56° C.; [α]$_{Hg436}$ = −4.5; (c = 1.5; DCM); IR (KBr): 3282, 2924, 2852, 1716, 1622, 1365, 1223 cm$^{-1}$; | 7.80 | 77.0 |

TABLE 12-continued

Chiral carriers and extractors based on 9,11-subst.-10,11-dihydrocinchonan derivatives used for stereoselective liquid—liquid extraction.

| R₁ | X | Y | R₄ | cinchona alkaloid precursor | physico-chemical properties of chiral extractors (9,11-subst.-DHC derivatives) | extraction experiments[a] q[b] | ee % |
|---|---|---|---|---|---|---|---|
| — | HO— | —S— | —(CH₂)₁₇—CH₃ | QN | m.p.: 84° C.; [α]$_{Hg546}$ = −120; (c = 1.0; DCM) IR (KBr): 2923, 1623, 1590, 1540 cm⁻¹; | 0.88[c] (1.14) | 7.0 |
| — | HO— | —C(=O)—CH(*)— | —(CH₂)₁₇—CH₃ | QN | m.p.: 86° C.; [α]$_{Hg546}$ = −51; (c = 1.0; DCM) IR (KBr): 2923, 1623, 1593, 1509 cm⁻¹; | 0.86[c] (1.16) | 8.0 |
| phenyl | —NH—C(=O)—O—CH₃ | — | — | QN | see Table 2 (this compound is not substituted at position 11) | 1.50 | 20.0 |
| phenyl | —NH—C(=O)—O—CH₃ | —S— | —(CH₂)₁₇—CH₃ | QN | yellow oil; [α]$_{Hg546}$ = +35.3; (c = 1.0; DCM) IR (KBr): 2926, 2854, 1734, 1624, 1603 cm⁻¹; | 2.24 | 38.3 |
| phenyl | —NH—C(=O)—O—CH₃ | —S— | —(CH₂)₁₇—CH₃ | QD | m.p.: 103; [α]$_{Hg546}$ = −0.9; (c = 1.0; DCM) IR (KBr): 2923, 2851, 1733, 1621, 1368, 1318 cm⁻¹; | 2.34 | 40.0 |
| phenyl | —NH—C(=O)—O—CH₃ | —C(=O)—CH(*)— | —(CH₂)₁₇—CH₃ | QN | yellow oil; [α]$_{Hg546}$ = −6.2; (c = 1.0; DCM) IR (KBr): 2925, 2854, 1731, 1620, 1363, 1318 cm⁻¹; | 2.60 | 44.4 |
| phenyl | —NH—C(=O)—O—CH₃ | —C(=O)—CH(*)— | —(CH₂)₁₇—CH₃ | QD | yellow oil; [α]$_{Hg546}$ = +15; (c = 1.0; DCM) IR (KBr): 3252, 2925, 1734, 1623, 1365 cm⁻¹; | | |
| tert-butyl (C(CH₃)₃) | —NH—C(=O)—O—CH₃ | —C(=O)—CH(*)— | —(CH₂)₁₇—CH₃ | QN | m.p.: 114–116° C.; [α]$_{Hg546}$ = −12.4; (c = 1.01; MeOH) IR (KBr): 3429, 2925, 2855, 1715, 1622, 1393, 1364 cm⁻¹; | | |
| tert-butyl | —NH—C(=O)—O—CH₃ | —S— | —(CH₂)₂—OH | QN | m.p.: 184–186° C.; [α]$_{Hg546}$ = −25.2; (c = 1.9; MeOH) IR (KBr): 2920, 2862, 1730, 1620, 1592, 1512, 1364, 1225 cm⁻¹; | | |
| tert-butyl | —NH—C(=O)—O—CH₃ | —S— | —(CH₂)₂—OH | CD | m.p.: 154–158° C.; [α]$_{Hg546}$ = −9.2; (c = 1.0; MeOH) IR (KBr): 3264, 2922, 1727, 1592, 1541 cm⁻¹; | | |
| tert-butyl | —NH—C(=O)—O—CH₃ | —C(=O)—CH(*)— | —(CH₂)₂—OH | QN | m.p.: 246° C.; [α]$_{Hg546}$ = −38.0; (c = 1.9; AcOH) IR (KBr): 2920, 2860, 1717, 1621, 1592, 1508, 1363, 1224 cm⁻¹; | | |
| —(CH₂)₁₁—CH₃ | —NH—C(=O)—O—CH₃ | —S— | —(CH₂)₁₁—CH₃ | QN | m.p.: 82–85° C.; [α]$_{Hg546}$ = −3.2; (c = 1.78; DCM) IR (KBr): 2922, 2852, 1721, 1622, 1592, 1543, 1511, 1464, 1262 cm⁻¹; | | |

TABLE 12-continued

Chiral carriers and extractors based on 9,11-subst.-10,11-dihydrocinchonan derivatives used for stereoselective liquid—liquid extraction.

| R$_1$ | X | Y | R$_4$ | cinchona alkaloid precursor | physico-chemical properties of chiral extractors (9,11-subst.-DHC derivatives) | extraction experiments[a] q[b] | ee % |
|---|---|---|---|---|---|---|---|
| —(CH$_2$)$_{11}$—CH$_3$ | carbamate NH | C(=O)O* (acetate) | —(CH$_2$)$_{11}$—CH$_3$ | QN | m.p.: 90–92° C.; [α]$_{Hg546}$ = −5.4; (c = 1.9; DCM) IR (KBr): 2924, 2853, 1721, 1622, 1591, 1543, 1511, 1261, 1035 cm$^{-1}$; | | |
| 3,5-dimethylphenyl | carbamate NH | C(=O)O* (acetate) | —(CH$_2$)$_{11}$—CH$_3$ | QN | yellow oil; [α]$_{Hg546}$ = +37; (c = 1.0; DCM) IR (NaCl): 2927, 2853, 1730, 1621, 1362 cm$^{-1}$; | | |

Dimeric extractors:

| t-butyl | carbamate NH | —S— | CH(CH$_3$)CH(OH)CH$_2$— OH | QN | m.p.:118–122° C.; [α]$_{Hg546}$ = −14; (c = 1.0; DCM) IR (KBr): 3418, 2927, 2869, 1719, 1623, 1593, 1510, 1365 cm$^{-1}$; | | |
| cyclohexyl | carbamate NH | —S— | —(CH$_2$)$_{11}$—CH$_3$ | QN | m.p.: 149–152° C.; [α]$_{Hg546}$ = +14; (c = 1.07; CHCl$_3$) IR (KBr): 2955, 1717, 1622, 1593, 1511 cm$^{-1}$; | 4.60 | 64.3 |
| 4-methylcyclohexyl | carbamate NH | C(=O)O* (acetate) | —(CH$_2$)$_{11}$—CH$_3$ | QN | m.p.: 166–170° C.; [α]$_{Hg546}$ = +10.3; (c = 1.0; CHCl$_3$) IR (KBr): 2926, 1716, 1622, 1593, 1511 cm$^{-1}$; | | |

[a]extraction experiments are performed with non-optimized condions with respect to organic solvent, carrier concentration and pH conditions
[b]q = ratio of enantiomers in organic phase
[c]reversal of elution and extraction selectivity

What is claimed is:

1. Compounds of the general formula (I):

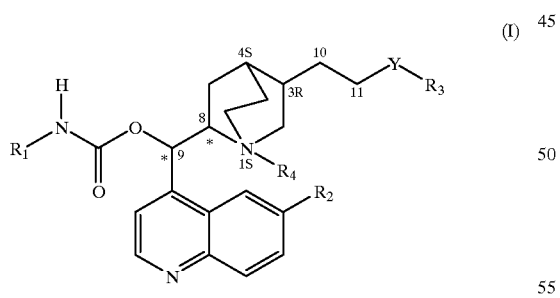

with the 9,11-substituted-10,11-dihydro-cinchonan skeleton (9,11-Subst.-DHC skeleton) and the stereoisomers resulting from the different configurations at positions 8 and 9 of the DHC skeleton, wherein Y is thio group ( thioether; S), the sulfinyl group (sulfoxide; SO) introducing a new chiral center or a sulfonyl group (sulfone; SO$_2$);

R$_1$ is an optionally substituted aliphatic, linear or branched, non-chiral or chiral C$_1$–C$_{18}$ residue selected from the group consisting of n-propyl, n-decyl, n-dodecyl, n-octadecyl, isopropyl, tert.-butyl, β-chloro-tert.-butyl, β,β'-dichloro-tert.-butyl, 2-hydroxy-1,2-diphenylethyl, 2-amino-1,2-diphenylethyl, (1S)- or (1R)-1-carboxy-3-methylbutyl or the methyl esters thereof, 3-trialkoxysilylpropyl, 3-trichlorosilylpropyl, 10-trialkoxysilyldecyl, 10-trichlorosilyldecyl, 3-(3-trialkoxysilylpropyl)thiopropyl, 3-(3-trialkoxysilylpropyl)sulfinylpropyl, 3-(3-trichlorosilylpropyl)thiopropyl, propylthiopropyl and 3-(3-trichlorosilylpropyl)sulfinylpropyl;

allyl;

phenylamino or 3,5-dinitrobenzoylamino an optionally substituted non-chiral or chiral alicyclic or heteroalicyclic residue selected from the group consisting of 1-adamantyl, 1-hydroxy-2-indanyl, cyclohexyl, 2-aminocyclohexyl, cyclohexenyl, 3-quinuclidinyl, cis or trans 2- or 4-carboxycyclohexyl or the methyl ester thereof, cis or trans 2- or 4-carboxycyclohexenyl or the methyl esters thereof and 3-cholesteryl;

an optionally substituted aromatic or heteroaromatic residue selected from the group consisting of 3,5-dinitrophenyl, 3,4-dichlorophenyl, 3,5-bis-(trifluoromethyl)phenyl, 4-methylphenyl, 3,5-- dimethylphenyl, 3,4,5-trimethoxyphenyl, 2,6-diisopropylphenyl, 1- or 2-naphthyl, 6-methoxy-4-chinolinyl, 2- or 3- or 4-carboxyphenyl and the methyl esters thereof;

an optionally substituted non-chiral or chiral arylalkyl residue selected from the group consisting of benzyl, di-phenylmethyl, triphenylmethyl, (R)- or (S)-α-methyl-benzyl, (R)- and (S)-1-(4-nitrophenyl)ethyl;

trialkylsilyl;

any one of the groups 3-tri-alkoxysilylpropyl, 3-trichlorosilylpropyl, 10-trialkoxysilyldecyl, 10-trichlorosilyldecyl, 3-(3-trialkoxysilyl-propyl) thiopropyl, 3-(3-trialkoxysilylpropyl)sulfinfylpropyl, 3-(3-trichlorosilylpropyl)thiopropyl, 3-(3-trichlorosilylpropyl)sulfinylpropyl or propylthiopropyl is optionally immobilized onto silica;

2-((meth)acryloyloxy)ethyl or (meth)acryloyl so that the 9,11-Subst.-DHC skeleton of formula (I) via $R_1$ may be polymerized or copolymerized with a comonomer selected from vinyl modified silica, (meth)acryl modified silica, 3-trialkoxysilylpropyl(meth)-acrylate, styrene, any (meth)acrylate, vinyl functionialized polysiloxane and any other olefin;

or a spacer selected from the group consisting of 1,4-tetramethylene, 1,6-hexamethylene, trans or cis 1,4- or 1,2-cyclohexylene, 1,2- or 1,3- or 1,4-phenylene, toluene-2,6-diyl, 3,3'-dimethoxy-biphenyl-4,4'-diyl (dianisidinediyl), 1,1'-binaphthyl-2,2'-diyl, 1,2-diphenylethan-1,2-diyl, phthalazin-1,4-diyl, adamantine-1,7-diyl, cyclohexan-1,3,5-triyl, benzene-1,3,5-triyl and adamantane-1,3,5,7-tetrayl connecting two, three or four 9,11-Subst.-DHC skeletons of formula (i) but missing $R_1$.

$R_2$ is hydrogen, hydroxy or a $C_1$–$C_{15}$ alkoxy or alicyclicoxy group; is hydrogen;

$R_3$ is hydrogen, an optionally substituted aliphatic linear or branched, chiral or non-chiral aliphatic $C_1$–$C_{18}$ or alicyclic residue selected from the group consisting of 2-hydroxyethyl, 2-alkoxyethyl, 2-(alkylcarbonyloxy)ethyl, 2-(alkylcarbamoyl-oxy)ethyl, 2-(N-alkyl substituted alkylcarbamoyloxy)ethyl, 2-(N-substituted amino)ethyl, 2-aminoethyl, octyl, dodecyl, octadecyl and cholesteryl;

2-((meth)acryloyloxy)ethyl or optionally N-alkyl 2-((meth)-acrylamido) ethyl so that the 9,11-Subst.-DHC skeleton of formula (I) via $R_3$ may be polymerized or copolymerized with other polymerizable comonomers;

3-trialkoxysilylpropyl, 3-trichlorosilylpropyl or propyl which are immobilized onto silica;

$R_4$ is missing thus signifying the free base, hydrogen in the case of ammonium salts, or methyl, allyl, arylmethyl or benzyl, in the case of quaternized salts.

2. Compounds according to claim 1, wherein the 9,11-Subst.-DHC skeleton of formula (I) is polymerized or copolymerized by addition polymerization wherein $R_1$ is tert-butyl and $R_3$ is 2-((meth)acryloyloxy) ethyl or wherein $R_1$ is 2-((meth)acryloyloxy)ethyl and $R_3$ is octadecyl.

3. Compounds according to claim 1, wherein $R_3$ is silicapropyl or $R_1$ is silicapropylthiopropyl.

4. Compounds according to claim 1, wherein Y, $R_1$ and $R_3$ have the following meanings:

| compound | Y | $R_1$ | $R_3$ |
|---|---|---|---|
| 1 | —S— | 1-adamantyl | octadecyl |
| 2 | —SO— | 1-adamantyl | octadecyl |
| 3 | $SO_2$ | 1-adamantyl | octadecyl |
| 4 | —S— | tert.-butyl | octadecyl |
| 5 | —SO— | tert.-butyl | octadecyl |
| 6 | —S— | tert.-butyl | —$(CH_2)_2$—OH |
| 7 | —SO— | tert.-butyl | —$(CH_2)_2$—OH |
| 8 | —SO— | 2,6-diisopropylphenyl | octadecyl |
| 9 | —SO— | 1-naphthyl | octadecyl |
| 10 | —S— | tert-butyl | —$(CH_2)_3$—Si—O-silica |
| 11 | —S— | 3,5-dinitrophenyl | —$(CH_2)_3$—Si—O-silica |
| 12 | —S— | 2,6-diisopropylphenyl | —$(CH_2)_3$—Si—O-silica |
| 13 | —S— | triphenylmethyl | —$(CH_2)_3$—Si—O-silica |
| 14 | —S— | (1S)-1-carboxy-3-methylbutyl | $(CH_2)_3$—Si—O-silica |
| 15 | —S— | (1R)-1-carboxy-3-methylbutyl | $(CH_2)_3$—Si—O-silica |
| 16 | —SO— | tert.-butyl | $(CH_2)_2$—O-polymethacrylate |
| 17 | —S— | 3-cholesteryl | $(CH_2)_3$—Si—O-silica | or wherein $R_1$ is a spacer selected from the groups 1,6-hexime-thylene, trans 1,4-cyclohexylene, 1,3-phenylene, (R,R) 1,-2-cyclohexylene and (S,S)-1,2-cyclohexylene; is the thio or sulfinyl group and $R_3$ is —$(CH_2)_3$—Si—O-Silica or octadecyl; and their respective salts.

5. A process for the enantioseparation of chiral neutral compounds with polar groups, chiral acidic compounds, chiral basic and amphoteric compounds wherein the chiral acidic compounds are selected from the group consisting of carboxylic acids, sulfonic acids, phosphoric acids, N-protected α-, β-, or γ-amino acids, (hetero)arylalkyl carboxylic acids, (hetero)aryloxy carboxylic acids, (hetero)arylthio carboxylic acids, substituted alicyclic carboxylic acids, α-, β- or alkyl alkanoic acids, (substituted) α-allyl or α-benzyl acetic acids, free α-, β-, or γ-amino acids, free peptides, N-derivatized peptides, NH-acidic benzimidazolyl sulfoxides, OH acidic coumarins, acidic compounds with imide structures, and acidic atropisomeric biphenyls or binaphthyls and wherein the basic and amphoteric compounds are Ca-antagonists, selected from the group consisting of veraparil, gallopamil and 1,4-dihydropyridine-3,5-dicarboxylic acid mono methyl esters; the process comprising the steps of contacting said compounds with at least one compound as recited in claim 1 to form diastereomeric molecule associates and of separating said diastereomeric molecule associates, the contacting and separating steps being performed by means of a) liquid phase separation techniques, which is liquid chromatography (LC), capillary electrophoresis (CE) or capillary electrochromatography (CEC), b) extraction methodology, which is liquid-liquid extraction, countercurrent related extraction, liquid-solid extraction technology, supported liquid membrane or fired site membrane technologies, or c) crystallization technology.

* * * * *